US007947256B2

(12) United States Patent
Rajopadhye et al.

(10) Patent No.: US 7,947,256 B2
(45) Date of Patent: May 24, 2011

(54) BIOCOMPATIBLE FLUORESCENT IMAGING AGENTS

(75) Inventors: Milind Rajopadhye, Westford, MA (US); Kevin Groves, Somerville, MA (US)

(73) Assignee: VisEn Medical, Inc., Waltham, MA (US)

( * ) Notice: Subject to any disclaimer, the term of this patent is extended or adjusted under 35 U.S.C. 154(b) by 0 days.

(21) Appl. No.: 12/065,385

(22) PCT Filed: Sep. 1, 2006

(86) PCT No.: PCT/US2006/034604
§ 371 (c)(1),
(2), (4) Date: Jul. 24, 2008

(87) PCT Pub. No.: WO2007/028163
PCT Pub. Date: Mar. 8, 2007

(65) Prior Publication Data
US 2008/0317676 A1 Dec. 25, 2008

Related U.S. Application Data

(60) Provisional application No. 60/714,075, filed on Sep. 2, 2005.

(51) Int. Cl.
*A61K 49/04* (2006.01)
(52) U.S. Cl. ......... 424/9.44; 424/9.1; 424/9.6; 548/449; 546/276.7; 546/269.4; 540/575
(58) Field of Classification Search ............ 424/9.44, 424/9.1, 9.6; 548/449; 546/276.7, 277.4; 540/575
See application file for complete search history.

(56) References Cited

U.S. PATENT DOCUMENTS

| | | | |
|---|---|---|---|
| 4,264,694 | A | 4/1981 | Pu et al. |
| 4,981,977 | A | 1/1991 | Southwick et al. |
| 5,073,171 | A | 12/1991 | Eaton |
| 5,268,486 | A | 12/1993 | Waggoner et al. |
| 5,569,766 | A | 10/1996 | Waggoner et al. |
| 5,593,658 | A | 1/1997 | Bogdanov et al. |
| 5,605,809 | A | 2/1997 | Komoriya et al. |
| 5,627,027 | A | 5/1997 | Waggoner |
| 5,808,044 | A | 9/1998 | Brush et al. |
| 5,877,310 | A | 3/1999 | Reddington et al. |
| 6,002,003 | A | 12/1999 | Shen et al. |
| 6,004,536 | A | 12/1999 | Leung et al. |

(Continued)

FOREIGN PATENT DOCUMENTS

EP 0417941 A2 3/1991

(Continued)

OTHER PUBLICATIONS

Becker et al. (2000) "Macromolecular Contrast Agents for Optical Imaging of Tumors: Comparison of Indotricarbocyanine-labeled Human Serum Albumin and Transferrin," *Photochom. Photobiol.* 72:234-241.

(Continued)

*Primary Examiner* — Yong Chu
*Assistant Examiner* — Valerie Rodriguez-Garcia
(74) *Attorney, Agent, or Firm* — Goodwin Procter LLP

(57) ABSTRACT

This invention relates to new carbocyanine fluorophores comprising a biomolecule targeting moiety containing 1-6 aromatic moieties, wherein the targeting moiety is designed to attach to biocompatible molecules to form in vivo optical imaging agents.

15 Claims, 1 Drawing Sheet

U.S. PATENT DOCUMENTS

| | | | |
|---|---|---|---|
| 6,008,373 | A | 12/1999 | Waggoner et al. |
| 6,027,709 | A | 2/2000 | Little et al. |
| 6,043,025 | A | 3/2000 | Minden et al. |
| 6,083,485 | A | 7/2000 | Licha et al. |
| 6,083,486 | A | 7/2000 | Weissleder et al. |
| 6,127,134 | A | 10/2000 | Minden et al. |
| 6,130,094 | A | 10/2000 | Waggoner et al. |
| 6,133,445 | A | 10/2000 | Waggoner et al. |
| 6,136,612 | A | 10/2000 | Della Ciana et al. |
| 6,248,904 | B1 | 6/2001 | Zhang et al. |
| 6,258,340 | B1 * | 7/2001 | Licha et al. |
| 6,448,008 | B1 * | 9/2002 | Caputo et al. ............ 435/6 |
| 6,534,041 | B1 | 3/2003 | Licha et al. |
| 6,592,847 | B1 | 7/2003 | Weissleder et al. |
| 6,740,755 | B2 | 5/2004 | Caputo et al. |
| 6,747,159 | B2 | 6/2004 | Caputo et al. |
| 6,869,593 | B2 | 3/2005 | Frangioni |
| 6,913,743 | B2 | 7/2005 | Licha et al. |
| 6,926,885 | B2 | 8/2005 | Licha et al. |
| 7,025,949 | B2 | 4/2006 | Licha et al. |
| 7,374,746 | B2 | 5/2008 | Frangioni |
| 7,445,767 | B2 | 11/2008 | Licha et al. |
| 7,647,091 | B2 | 1/2010 | Ntziachristos et al. |
| 7,655,217 | B2 | 2/2010 | Licha et al. |
| 2003/0044353 | A1 | 3/2003 | Weissleder et al. |
| 2005/0169843 | A1 | 8/2005 | Weissleder et al. |
| 2006/0099712 | A1 | 5/2006 | Gilman et al. |
| 2006/0275775 | A1 | 12/2006 | Weissleder et al. |
| 2008/0102036 | A1 | 5/2008 | Poss et al. |
| 2008/0226562 | A1 | 9/2008 | Groves et al. |
| 2008/0267883 | A1 | 10/2008 | Rajopadhye et al. |
| 2008/0286207 | A1 | 11/2008 | Narayanan |
| 2008/0312540 | A1 | 12/2008 | Ntziachristos |
| 2008/0317676 | A1 | 12/2008 | Rajopadhye et al. |
| 2009/0068115 | A1 | 3/2009 | Gaw et al. |
| 2009/0123383 | A1 | 5/2009 | Frangioni |
| 2009/0220430 | A1 | 9/2009 | Rajopadhye et al. |
| 2010/0074847 | A1 | 3/2010 | Madden et al. |
| 2010/0078576 | A1 | 4/2010 | Ntziachristos et al. |
| 2010/0129293 | A1 | 5/2010 | Licha et al. |
| 2010/0166659 | A1 | 7/2010 | Licha et al. |
| 2010/0172841 | A1 | 7/2010 | Peterson et al. |
| 2010/0189657 | A1 | 7/2010 | Weissleder et al. |

FOREIGN PATENT DOCUMENTS

| | | |
|---|---|---|
| EP | 0820057 A1 | 1/1998 |
| EP | 1065250 A1 | 1/2001 |
| EP | 1090961 A1 | 4/2001 |
| EP | 1219626 A1 | 7/2002 |
| JP | 10071766 A | 3/1998 |
| WO | WO-9740104 A1 | 10/1997 |
| WO | WO-9931181 A1 | 6/1999 |
| WO | WO-9951702 A1 | 10/1999 |
| WO | WO-00/16810 A1 | 3/2000 |
| WO | WO-0121624 A1 | 3/2001 |
| WO | WO-2007/028163 A1 | 3/2007 |
| WO | WO-2009114776 A2 | 9/2009 |

OTHER PUBLICATIONS

Brasseur et al. (1999) "Receptor-Mediated Targeting of Phthalocyanines to Macrophages via Covalent Coupling to Native or Maleylated Bovine Serum Albumin," *Photochem. Photobiol.* 69:345-353.

Gatter et al. (1983) "Transferrin Receptors in Human Tissues: Their Distribution and Possible Clininical Relevance," *J. Clin. Path.* 36:539-545.

Hamblin et al. (1994) "Photosensitizer Targeting in Photodynamic Therapy. I. Conjugates of Haematoporphyrin with Albumin and Transferrin," *J. Photochem Photobiol. B*. 26(1):45-56.

Hansch et al. (2004) "Diagnosis of Arthritis Using Near-Infrared Fluorochrome Cy5.5," *Investigative Radiology* 39(10):626-632.

Kremer et al. (2000) "Laser-Induced Fluorescence Detection of Malignant Gliomas Using Fluorescein-labeled Serum Albumin: Experimental and Preliminary Clinical Results," *Neurol. Res.* 22(5):481-489.

Montet et al. (2006) "An Albumin-Activated Far-Red Fluorochrome for In Vivo Imaging," *Chem Med Chem* 1(1):66-69.

Parmelee et al. (1997) "Preclinical Evaluation of the Pharmokinetics, Biodistribution and Elimination of MS-325, a Blood Pool Agent for Magnetic Imaging Resonance," *Investigative Radiology* 32(12):741-747.

Rennen et al. (2001) "The Effect of Molecular Weight on Nonspeciific Accumulation of (99m) T-Labeled Proteins in Inflammatory Foci," *Nucl. Med. Biol*. 28(4):401-408.

Schilling et al. (1992) "Design of Compounds Having Enhanced Tumour Uptake, Using Serum Albumin as a Carrier—Part II. In Vivo Studies," *Int. J. Rad. Appl. Instrum. B*. 19(6):685-695.

Tromberg et al. (1997) "Non-invasive measurements of breast tissue optical properties using frequency-domain photo migration," *Phil. Trans. R. Soc. London B* 352:661-668.

Wang et al. (2001) "Amplified Delivery of Indium-111 to EGFR-Positive Human Breast Cancer Cells," *Nucl. Med. Biol*. 28:895-902.

Williams et al. (1993) "Comparison of Covalent and Noncovalent Labeling with Near-Infrared Dyes for the High-Performance Liquid Chromatographic Determination of Human Serum Albumin," *Anal. Chem*. 65:601-605.

Wyatt (1997) "Cerebral oxygenation and haemodynamics in the fetus and newborn infant," *Phil. Trans. R. Soc. London B* 352:697-700.

Ciernik et al. (1972) "New synthesis of neocyanine dyes containing three heterocycles," *Collection of Czechoslovak Chemical Communications* 37(11):3800-3807. Abstract only.

Ciernik et al. (1972) "New pentamethinecyanine dyes," *Collection of Czechoslovak Chemical Communications* 37(8):2771-2778. Abstract only.

International Search Report and Written Opinion for International Patent Application No. PCT/US2006/034604, dated Jan. 31, 2007, 11 pages.

Bredereck et al. (1970) "Syntheses in the heterocyclic series. XIV. Formylation of 4-methylpyrimidine and reactions of 2-(4-pyrimidinyl)malonaldehyde," *Justus Liebigs Annalen der Chemie* 737:46-52. Abstract only.

Ernst et al. (1989) "Cyanine Dye Labelling Reagents for Sulphydryl Groups", *Cytometry*, 10:3-10.

Ficken, (1971) "The Chemistry of Synthetic Dyes", vol. 4, K. Venkataraman Ed., Academic Press, New York, p. 211-223.

Fry (1977) "Rodd's Chemistry of Carbon Compounds", "Cyanine Dyes and Related Compounds", Elsevier, Amsterdam. vol. IVb, Chapter 15, p. 369-424.

International Search Report and Written Opinion for International Patent Application No. PCT/US2006/034260, dated Jan. 31, 2007, 9 pages.

Lindsey et al. (1989) Visible Light Harvesting in Covalently-Linked Porphyrin Cyanine Dyes, *Tetrahedron*, 45:4845-4866.

Mujumdar et al. (1989) "Cyanine Dye Labelling Reagents Containing Isothiocyanate Groups", *Cytometry*, 10:11-19.

Mujumdar et al. (1993) "Cyanine Dye Labelling Reagents: Sulfoindocyanine Succinimidyl Esters", *Bioconjugate Chemistry*, 4:105-111.

Mujumdar et al. (1996) "Cyanine Labelling Reagents: sulfobenzoindocyanine succinimidyl esters", *Bioconjugate Chemistry*, 7:356-362.

Ozmen et al. (2000) "Infrared fluorescence sensing of submicromolar calcium: pushing the limits of photoinduced electron transfer," *Tetrahedron Letters* 41:9185-9188.

Sun et al. (2006) "'Clickable' Nanoparticles for Targeted Imaging," *Molecular Imaging* 5(2):122-128.

\* cited by examiner

BIOCOMPATIBLE FLUORESCENT IMAGING AGENTS

RELATED APPLICATION

This application is a national stage of International (PCT) Patent Application Serial No. PCT/US2006/034604, filed Sep. 1, 2006, and published under PCT Article 21(2) in English, which claims the benefit of U.S. Provisional Application No. 60/714,075, filed on Sep. 2, 2005.

The entire teachings of the above application are incorporated herein by reference.

BACKGROUND OF THE INVENTION

Near infrared wavelengths (approx. 600-1000 nm) have been used in optical imaging of internal tissues, because near infrared radiation exhibits tissue penetration of up to 15 centimeters. See, e.g., Wyatt, 1997, "Cerebral oxygenation and haemodynamics in the fetus and newborn infant," Phil. Trans. R. Soc. London B 352:701-706; and Tromberg et al., 1997, "Non-invasive measurements of breast tissue optical properties using frequency-domain photo migration," Phil. Trans. R. Soc. London B 352:661-667.

Advantages of near infrared imaging over other currently used clinical imaging techniques include the following: potential for simultaneous use of multiple, distinguishable probes (important in molecular imaging); high temporal resolution (important in functional imaging); high spatial resolution (important in in vivo microscopy); and safety (no ionizing radiation).

In near infrared fluorescence imaging, filtered light or a laser with a defined bandwidth is used as a source of excitation light. The excitation light travels through body tissues. When it encounters a near infrared fluorescent molecule ("contrast agent" or "probe"), the excitation light is absorbed. The fluorophore then emits light that has detectably different properties (i.e., spectral properties of the probe (slightly longer wavelength), e.g., fluorescence) from the excitation light.

SUMMARY OF THE INVENTION

The invention is based on the design of fluorophores that are capable of being taken up by, retained by or attached to a biocompatible molecule to form an in vivo imaging construct. The invention is also based on a fluorophore of the formula T-F wherein, T is an organic moiety that contains 1-6 aromatic moieties, including but not limited to phenyl moieties, substituted phenyl moieties and heterocyclic moieties. F is any fluorophore, fluorochrome, near infrared fluorophore or fluorochrome, or any carbocyanine fluorochrome. The invention is also based on the applications of these fluorophores for in vivo imaging applications.

In one embodiment, the present invention is directed to a fluorophore that when administered to a subject attaches to an endogenous biocompatible molecule in situ to form an in vivo imaging agent.

In another embodiment the present invention is directed to a compound represented by the following structural formula:

$$T_n\text{-}F$$

wherein:
T contains one or more aromatic groups;
F is a fluorophore; and
n is a positive integer from 1 to 5;
with the proviso that the compound is not:

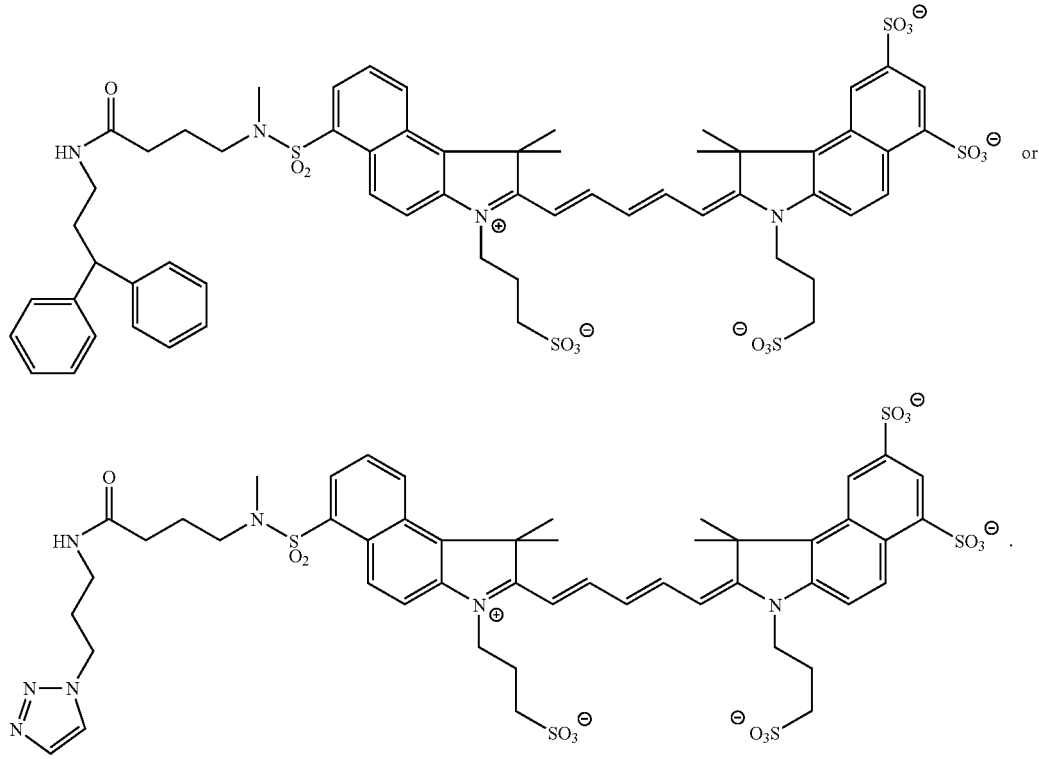

In another embodiment the present invention is directed to a compound represented by the following structural formula:

T-F wherein:
T contains one or more aromatic groups; and
F is a fluorophore.

In another embodiment the present invention is directed to a compound represented by the following structural formula:

(T)$_2$-F wherein F is a fluorochrome represented by structural formula (3):

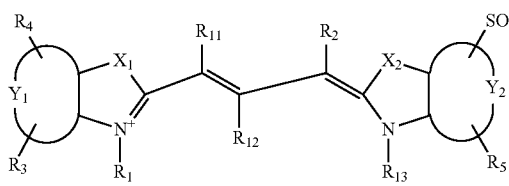

(3)

or a salt thereof, wherein:

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, F, Br, Cl, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;

wherein, $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety, a sulphonate moiety and the moiety $SO_2NR_6$-Q-CHR$_7$—[(CH$_2$)$_m$—W—(CH$_2$)$_p$—(O)$_k$]$_h$(CH$_2$)$_d$Z;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR*, when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or $R_6$ and $R_7$, taken together form a 4-, 5-, 6- or 7-membered heterocyclic or non-aromatic heterocyclic ring optionally substituted with halogen, OR*, N(R*)$_2$ or SR*; or $NR_6$, Q and CHR$_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$-Q-CHR$_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In another embodiment the present invention is a method of in vivo optical imaging, the method comprising:

(a) administering to a subject a fluorophore of the present invention;

(b) allowing the fluorophore time to attach to the biocompatible molecule and form an in vivo imaging agent;

(c) illuminating the subject with light of a wavelength absorbable by the fluorophore; and (e) detecting the optical signal emitted by the fluorophore.

In another embodiment the present invention is directed to a compound of formula (7) or a salt thereof

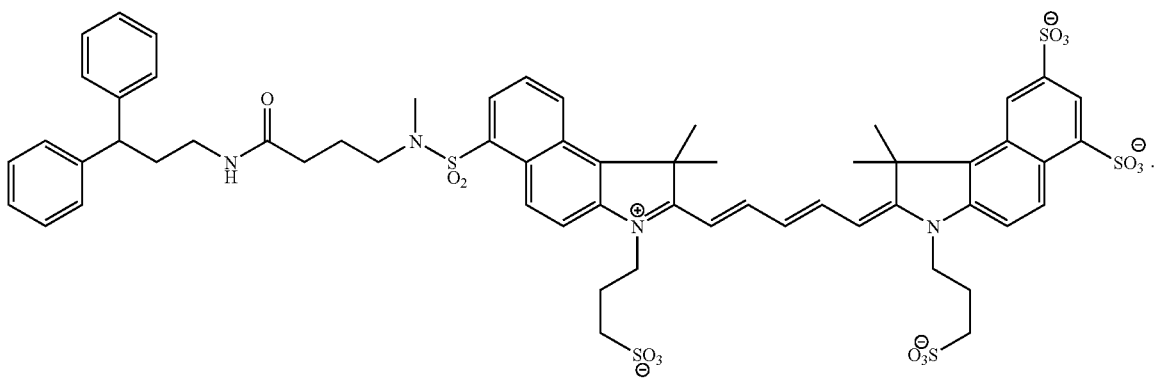

(7)

DETAILED DESCRIPTION OF THE INVENTION

Figure 1:
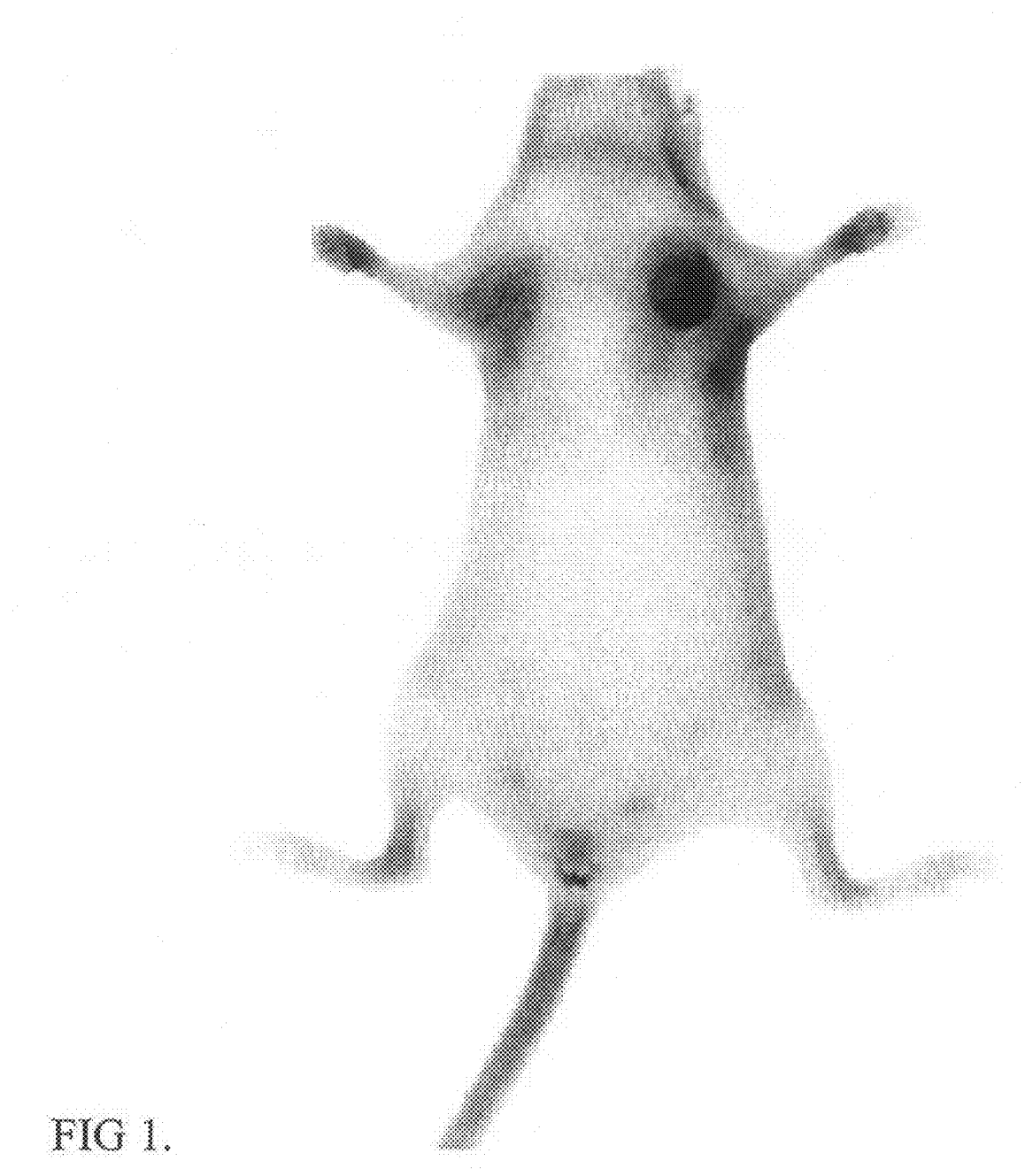
FIG. 1 is a fluorescence image of a compound of the present invention in tumors of a female NU/NU mice (6-8 weeks old) after 24 hrs on a fluorescence reflectance system (FRI, Kodak 2000MM) system.

A description of preferred embodiments of the invention follows.

The invention is based on the design of compounds (fluorophores) that are capable of being taken up by, retained by or attached to a biocompatible molecule to form an in vivo imaging construct.

The term "compounds," as used herein, refers to "polymethine fluorochromes", "fluorocliromes", "fluorescent dyes", "cyanine dyes" "carbocyanine dyes" and "dyes" of the instant invention. These terms are used interchangeably to refer to the compounds of the instant invention.

In one aspect of the invention, the compound (fluorophore) of the present invention comprises a biomolecule targeting moiety that allows the fluorophore to chemically link to the biomolecule (biocompatible molecule) (B). In one embodiment T is a biomolecule targeting moiety. As used herein the terms, "biomolecule" and "biocompatible molecule" can be used interchangeably to represent (B).

In certain embodiments a biomolecule targeting moiety is a moiety which will itself chemically bind, or cause the compound (fluorophore) to chemically bind, or cause the combination of the biomolecule targeting moiety and the compound (fluorophore) to chemically bind to a miomolecule.

In another aspect of the invention, the fluorescence intensity of the fluorophore is enhanced when chemically linked to a biomolecule (biocompatible molecule) (B). In certain embodiments of the present invention, when B is chemically linked to a compound of the present invention the fluorescence (fluorescence intensity) of the compound of the present invention is enhanced. In certain embodiments the fluorescence is enhanced by about 10%, about 25%, about 50% or more than about 50% which compared with the unlinked compound.

"Chemically linked" means connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions. This also includes crosslinking or caging.

In one aspect the compound of the present invention (fluorophore) is of the formula (1) or a salt thereof:

T-F (1)

In one aspect, T is an organic moiety that contains 1-6 aromatic moieties. In one aspect, T is an organic moiety that contains three aromatic moieties. In one aspect, T is an organic moiety that contains two aromatic moieties. In one aspect, T is an organic moiety that contains three phenyl moieties. In one aspect, T is an organic moiety that contains two phenyl moieties. In one aspect, T is an organic moiety that contains two substituted-phenyl moieties. In one aspect, T is an organic moiety that contains heterocyclic moieties. In one aspect, T is an organic moiety, independently taken from the following:

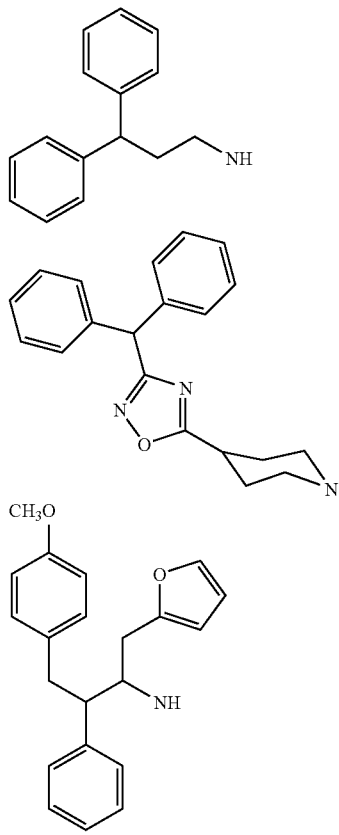

-continued

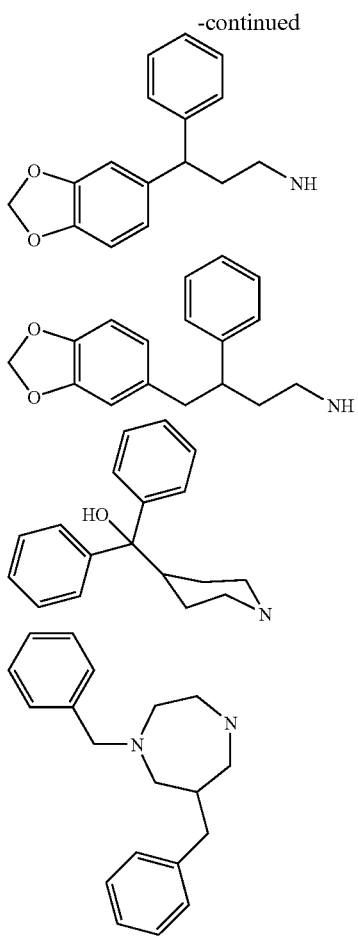

In one embodiment T has a molecular weigh of less than 500 Dalton.

In one aspect, F is any near infrared fluorophore or fluorochrome. In one embodiment F is any bright, highly fluorescent compounds (dyes) that absorb and/or emit between about 440 and about 1100 nm, between about 550 and about 800 nm, between about 500 and about 900 nm or between about 600 and about 900 nm and conjugates thereof. It will be appreciated that compounds (fluorochromes) with excitation and emission wavelengths in other spectrums, such as the visible and ultraviolet light spectrum, are also encompassed by the present invention.

In one aspect, F is any carbocyanine fluorochrome. In one aspect, F is selected from the formula:

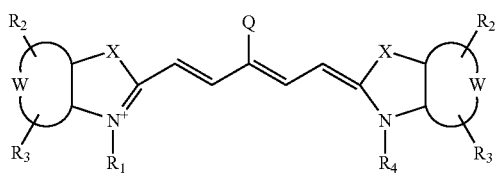

(2)

or a salt thereof, wherein:

X is independently selected from $C(CH_2Y_1)(CH_2Y_2)$, O, S, Se;

$Y_1$ and $Y_2$ are independently selected from H and $C_1$-$C_{20}$ alkyl that is linear or branched, saturated or unsaturated, optionally containing N, S, O in various forms;

W represents non-metal atoms required to form a benzo-condensed, a naphtho-condensed or a pyrido-condensed ring;

$R_1$ is selected from the group consisting of $(CH_2)_nCH_3$, $(CH_2)_nSO_3$— and $(CH_2)_nSO_3H$, wherein n is an integer selected from 0 to 6 when $R_1$ is $(CH_2)_nCH_3$, and n is an integer selected from 2 to 6 when $R_1$ is $(CH_2)_nSO_3$— or $(CH_2)_nSO_3H$;

$R_4$ is selected from the group consisting of $(CH_2)_nCH_3$, $(CH_2)_nSO_3$— and $(CH_2)_nSO_3H$, wherein n is an integer selected from 0 to 6 when $R_4$ is $(CH_2)_nCH_3$, and n is an integer selected from 2 to 6 when $R_4$ is $(CH_2)_nSO_3$— or $(CH_2)_nSO_3H$;

$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from a group consisting of a carboxyl functionalized heterocyclic ring;

Q is selected from a group consisting of a carboxyl functionalized nitrogen containing heterocyclic ring;

Q is selected from a group consisting of a carboxyl functionalized nitrogen containing 6-membered heterocyclic ring, such as pyridine, pyrimidone, pyrazine, and pyridazine;

Q is selected from a group consisting of a carboxyl functionalized nitrogen containing 6-membered heterocyclic ring, such as pyridine;

Q is selected from a group consisting of a carbonyl functionalized nitrogen containing 6-membered heterocyclic ring, such as pyridine;

Q is selected from a group consisting of isonicotinic acid, nicotinic acid and picolinic acid;

Q is selected from the groups shown:

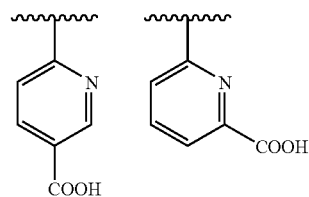

wherein the carboxyl group is also in the form of an ester, an activated ester or carbonyl halide that is capable of reacting with nucleophiles;

the carboxyl group is also in a form selected from the group CO—Obenzotriazolyl, CO—ON-succinimidyl, CO—Otetrafluorophenyl, CO—Opentafluorophenyl, CO—Oimidazolyl, CO—Op-nitrophenyl.

In one aspect, F is any carbocyanine fluorochrome. In one aspect, F is selected from the formula:

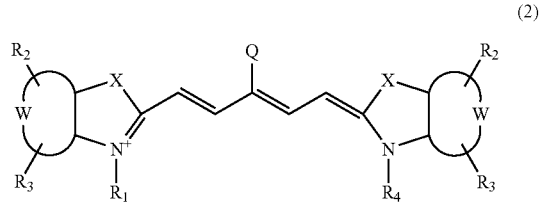

(2)

or a salt thereof, wherein:

X is independently selected from $C(CH_2Y_1)(CH_2Y_2)$, O, S, Se;

$Y_1$ and $Y_2$ are independently selected from H and $C_1$-$C_{20}$ alkyl that is linear or branched, saturated or unsaturated, optionally containing N, S, O in various forms;

W represents non-metal atoms required to form a benzo-condensed, a naphtho-condensed or a pyrido-condensed ring;

$R_1$ is selected from the group consisting of H, $(CH_2)_nCH_3$, $(CH_2)_nSO_3$— and $(CH_2)_nSO_3H$, wherein n is an integer selected from 0 to 6 when $R_1$ is $(CH_2)_nCH_3$, and n is an integer selected from 2 to 6 when $R_1$ is $(CH_2)_nSO_3$— or $(CH_2)_nSO_3H$;

$R_4$ is selected from the group consisting of H, $(CH_2)_nCH_3$, $(CH_2)_nSO_3$— and $(CH_2)_nSO_3H$, wherein n is an integer selected from 0 to 6 when $R_4$ is $(CH_2)_nCH_3$, and n is an integer selected from 2 to 6 when $R_4$ is $(CH_2)_nSO_3$— or $(CH_2)_nSO_3H$;

$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from a group consisting of a carboxyl functionalized heterocyclic ring;

Q is selected from a group consisting of a carboxyl functionalized nitrogen containing heterocyclic ring;

Q is selected from a group consisting of a carboxyl functionalized nitrogen containing 6-membered heterocyclic ring, such as pyridine, pyrimidone, pyrazine, and pyridazine;

Q is selected from a group consisting of a carboxyl functionalized nitrogen containing 6-membered heterocyclic ring, such as pyridine;

Q is selected from a group consisting of a carbonyl functionalized nitrogen containing 6-membered heterocyclic ring, such as pyridine;

Q is selected from a group consisting of isonicotinic acid, nicotinic acid and picolinic acid;

Q is selected from the groups shown:

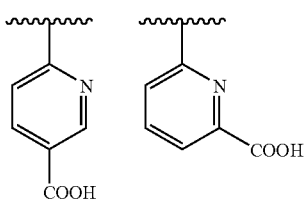

wherein the carboxyl group is also in the form of an ester, an activated ester or carbonyl halide that is capable of reacting with nucleophiles;

the carboxyl group is also in a form selected from the group CO—Obenzotriazolyl, CO—ON-succinimidyl, CO—Otetrafluorophenyl, CO—Opentafluorophenyl, CO—Oimidazolyl, CO—Op-nitrophenyl.

In certain embodiments, when F is formula (2) T is attached to the variable Q

Compounds of the general formula (2) are described in PCT Application Titled: Nicotinic Acid And Picolinic Acid Derived Near-Infrared Fluorophores, by Rajopadhye, Milind et al., filed Sep. 1, 2006, the entire contents of which are incorporated herein by reference.

Thus, in one aspect, the fluorophores (F) of the present invention are further substituted one or more times by sulfo or sulfoalkyl. By "sulfo" is meant sulfonic acid, or salt of sulfonic acid (sulfonate). Similarly, by "carboxyl" is meant carboxylic acid, carboxylate ester or salt of carboxylic acid. "Phosphate" is an ester of phosphoric acid, and includes salts of phosphate. "Phosphonate" means phosphonic acid and includes salts of phosphonate. Similarly for "carbonyl" groups such as, but not limited to carbonyl halode, (e.g., chloride) and carboxamide are included. As used herein, unless otherwise specified, the alkyl portions of substituents such as alkyl, alkoxy, arylalkyl, alkylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfo, amino, or hydroxy.

In another embodiment, the present invention provides compounds representing F by the formula (2):

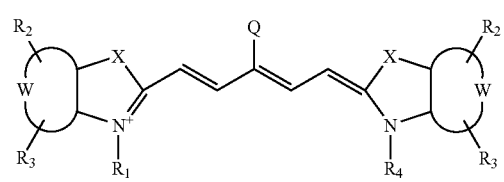

(2)

wherein, W represents non-metal atoms required to form a benzo-condensed, a naphtho-condensed or a pyrido-condensed ring.

In one aspect W represents the atoms necessary to form one to two fused aromatic rings having 6 atoms in each ring, which atoms are selected from —CH, —C, —$CR_7$, and —$NR_8$, where $R_8$ is 0 or 1 (such that each ring nitrogen is either quaternized or not), and each $R_7$ independently contains sulfo, trifluoromethyl, or halogen; $R_8$ independently contains a $C_1$-$C_8$ alkyl, in turn containing independently an H, amino or sulfo.

Incorporation of one or more non-hydrogen substituents on the fused rings can be used to tune the absorption and emission spectrum of the resulting dye.

Selected examples of the basic structure of $Z^1$ and $Z^2$ are shown below. These basic structures (3-6) are optionally further substituted as described in this section.

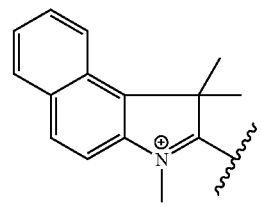

(8)

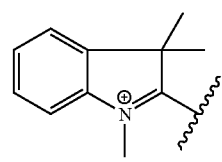

(9)

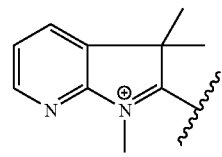

(10)

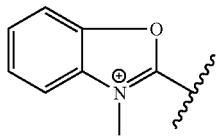
(11)

In one embodiment, X is independently selected from O, S, Se, —C(CH$_2$Y$_1$)(CH$_2$Y$_2$), wherein Y$_1$ and Y$_2$ are independently selected from H and C$_1$-C$_{20}$ alkyl that is linear or branched, saturated or unsaturated, optionally containing N, S, O in various forms, In another embodiment Y$_1$ and Y$_2$ together are part of a cyclic ring; or X is independently selected from —CR$_5$R$_6$, wherein R$_5$ and R$_6$, which may be the same or different, are alkyl, cycloalkyl, or arylalkyl, together part of a cyclic system and optionally further substituted.

In one aspect of the invention, R$_2$ and R$_3$ taken in combination complete a five or six-membered ring.

The substituent R$_1$ is typically selected from the group consisting of (CH$_2$)$_n$CH$_3$, (CH$_2$)$_n$SO$_3^-$ and (CH$_2$)$_n$SO$_3$H, wherein n is an integer selected from 0 to 6 when R$_1$ is (CH$_2$)$_n$CH$_3$, and n is an integer selected from 2 to 6 when R$_1$ is (CH$_2$)$_n$SO$_3^-$ or (CH$_2$)$_n$SO$_3$H. In one aspect, R$_1$ is (CH$_2$)$_3$SO$_3^-$ or (CH$_2$)$_4$SO$_3^-$ or CH$_2$CH$_3$. In one aspect of the invention R$_1$ is a substituent containing an aryl sulfonate or an amino group or a phthalimido group.

The substituent R$_1$ is typically selected from the group consisting of H, (CH$_2$)$_n$CH$_3$, (CH$_2$)$_n$SO$_3^-$ and (CH$_2$)$_n$SO$_3$H, wherein n is an integer selected from 0 to 6 when R$_1$ is (CH$_2$)$_n$CH$_3$, and n is an integer selected from 2 to 6 when R$_1$ is (CH$_2$)$_n$SO$_3^-$ or (CH$_2$)$_n$SO$_3$H. In one aspect, R$_1$ is (CH$_2$)$_3$SO$_3^-$ or (CH$_2$)$_4$SO$_3^-$ or CH$_2$CH$_3$. In one aspect of the invention R$_1$ is a substituent containing an aryl sulfonate or an amino group or a phthalimido group.

The substituent R$_4$ is typically selected from the group consisting of (CH$_2$)$_n$CH$_3$, (CH$_2$)$_n$SO$_3^-$ and (CH$_2$)$_n$SO$_3$H, wherein n is an integer selected from 0 to 6 when R$_4$ is (CH$_2$)$_n$CH$_3$, and n is an integer selected from 2 to 6 when R$_4$ is (CH$_2$)$_n$SO$_3^-$ or (CH$_2$)$_n$SO$_3$H. In one aspect, R$_4$ is (CH$_2$)$_3$SO$_3^-$ or (CH$_2$)$_4$SO$_3^-$ or CH$_2$CH$_3$. In one aspect of the invention R$_4$ is a substituent containing an aryl sulfonate or an amino group or a phthalimido group.

The substituent R$_4$ is typically selected from the group consisting of H, (CH$_2$)$_n$CH$_3$, (CH$_2$)$_n$SO$_3^-$ and (CH$_2$)$_n$SO$_3$H, wherein n is an integer selected from 0 to 6 when R$_4$ is (CH$_2$)$_n$CH$_3$, and n is an integer selected from 2 to 6 when R$_4$ is (CH$_2$)$_n$SO$_3^-$ or (CH$_2$)$_n$SO$_3$H. In one aspect, R$_4$ is (CH$_2$)$_3$SO$_3^-$ or (CH$_2$)$_4$SO$_3^-$ or CH$_2$CH$_3$. In one aspect of the invention R$_4$ is a substituent containing an aryl sulfonate or an amino group or a phthalimido group.

The substituents R$_2$ and R$_3$ are independently selected from the group H, halogens, carboxylate, carboxylic acid, carboxylic esters, amino, amide, alkyl or aryl sulfonamide, hydroxy, alkoxy, aryloxy, sulfate, cyano, nitro, azido, alkylamino, dialkylamino, trialkylammonium, phosphate, phosphate ester, phosphonate, sulphonic acid and a sulphonate moiety. In certain embodiments, R$_2$ and R$_3$ are independently, sulphonic acid or a salt thereof.

In one aspect of the invention, R$_2$ and R$_3$ could imply per-substitution, as in per-fluorinated W. Per-fluorination or poly-fluorination can lead to enhancement of fluorescence quantum yield.

As used herein "enhancement" means an increase in the fluorescence quantum yield, by about 5%, about 10%, about 15%, about 25%, about 50%, about 80%, about 90% about 95% about 98% about 99% about 100%.

In one aspect of the invention, the formula (2) is represented according to the formula (12):

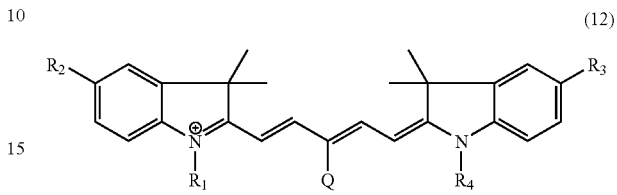
(12)

In one aspect of the invention, the compounds of the invention represented by (F), for example, formula (2) are sulfonated one or more times. If F is substituted by sulfo, it is typically sulfonated at R$_2$ or R$_3$ or both, (that is, for example, R$_2$ and/or R$_3$ are a sulfonic acid moiety, sulfonate moiety or sulfonamamide) or sulfoalkylated at R$_1$ or R$_4$ or both (that is, for example, R$_1$ and/or R$_4$ are (CH$_2$)$_n$SO$_3^-$ or (CH$_2$)$_n$SO$_3$H), or is both sulfonated and sulfoalkylated. In a particular embodiment, the compounds are sulfonated up to three times (at positions corresponding to R$_2$ and R$_3$, and as sulfoalkyl at one of R$_1$ or R$_4$), leaving one of R$_1$ or R$_4$ for the location of a reactive group.

As used herein the terms sulfonic acid and (CH$_2$)$_n$SO$_3$H or a sulfonate group and (CH$_2$)$_n$SO$_3^-$ can be used interchangeably. However in certain embodiments the terms a sulfonic acid moiety, sulfonate moiety or sulfonamamide refer to substituents which are attached to the remainder of the molecule by the a sulfonic acid moiety, sulfonate moiety or sulfonamamide moiety, i.e., —SO2NR'R"

In certain embodiments, at least one of R$_1$ to R$_3$ is or contains a sulphonic acid moiety or a sulphonate moiety. In certain embodiments, at least one of R$_1$ to R$_3$ is a sulphonic acid moiety or a sulphonate moiety.

In certain embodiments, R$_1$ and R$_4$ are independently (CH$_2$)$_n$SO$_3^-$ or (CH$_2$)$_n$SO$_3$H.

In one embodiment of the present invention the compounds are sulfonated up to four times (at R$_2$ and R$_3$, and as sulfoalkyl at R$_1$ and R$_4$). In another embodiment of the present invention the compounds are sulfonated at least four times (at R$_2$ and R$_3$, and as sulfoalkyl at R$_1$ and R$_4$). In another embodiment of the present invention, any reactive group (or chemically linked molecule) can be attached at Q, in addition the compounds of the present invention being sulfonated up to four times (at R$_2$ and R$_3$, and as sulfoalkyl at R$_1$ and R$_4$). In another embodiment of the present invention, any reactive group (or chemically linked molecule) can be attached at Q, in addition the compounds of the present invention being sulfonated at least four times (at R$_2$ and R$_3$, and as sulfoalkyl at R$_1$ and R$_4$). This extra sulfonation, as well as the change in attachment site, results in reactive dyes and dye conjugates that are brighter, more soluble in aqueous solutions, and more resistant to the fluorescence quenching that results from dye-dye stacking interactions.

In one aspect of the invention, the formula (2) is represented according to the formula (13):

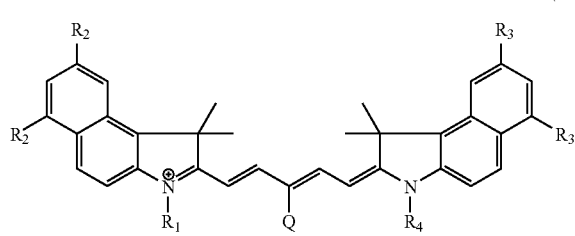

(13)

In one aspect of the invention, the compounds of the invention that are sulfonated one or more times are typically sulfonated at $R_2$ or $R_3$, or sulfoalkylated at $R_1$ or $R_4$ or both, or is both sulfonated and sulfoalkylated. In particular, the compounds of the present invention are sulfonated up to four times leaving one of $R_1$ or $R_4$ for the location of a reactive group.

In one embodiment of the present invention the compounds are sulfonated up to six times (at $R_2$ and $R_3$, and as sulfoalkyl at $R_1$ and $R_4$). In another embodiment of the present invention the compounds are sulfonated at least six times (at $R_2$ and $R_3$, and as sulfoalkyl at $R_1$ and $R_4$). In another embodiment of the present invention, any reactive group (or chemically linked molecule) can be attached at Q, in addition the compounds of the present invention being sulfonated up to six times (at $R_2$ and $R_3$, and as sulfoalkyl at $R_1$ and $R_4$). In another embodiment of the present invention, any reactive group (or chemically linked molecule) can be attached at Q, in addition the compounds of the present invention being sulfonated at least six times (at $R_2$ and $R_3$, and as sulfoalkyl at $R_1$ and $R_4$). This extra sulfonation, as well as the change in attachment site, results in reactive dyes and dye conjugates that are brighter, more soluble in aqueous solutions, and more resistant to the fluorescence quenching that results from dye-dye stacking interactions.

In one embodiment, the PML moiety has the formula (14):

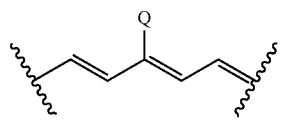

(14)

wherein Q is selected from a group consisting of carboxyl functionalized heterocyclic ring (heteroaryl substituted with a carboxy group). In this embodiment, heterocyclic ring and heteroaryl ring refers to heteroaryl ring as defined herein, such as pyridine and functionalized refers to substituted.

Suitable examples of appropriate PML moieties for compounds of the present invention (carbocyanine dyes) have been described in the literature, including PML moieties that incorporate nonhydrogen substituents, ring structures, and rigidizing elements (U.S. Pat. No. 5,831,098 to Ollmann, Jr (1998); U.S. Pat. No. 6,086,737 to Patonay et al. (2000); U.S. Pat. No. 6,048,982 to Waggoner (2000); and U.S. Pat. No. 5,453,505 to Lee et al. (1995); U.S. Pat. No. 5,639,874 to Middendorf et al. (1997); U.S. Pat. No. 3,864,644 to Lincoln et al (1975); U.S. Pat. No. 4,011,086 to Simson (1977); U.S. Pat. No. 6,747,159 to Caputo (2004); all incorporated herein by reference in their entirety).

In one embodiment the invention is directed to a PML of the formula (14), wherein Q is selected from a group consisting of a functionalized nitrogen-containing heterocyclic ring. One aspect of the invention is a PML of the formula (14), wherein Q is selected from a group consisting of a substituted nitrogen-containing heteroaryl ring. In these embodiments, heterocyclic ring and heteroaryl ring refers to heteroaryl ring as defined herein, such as pyridine, and functionalized refers to substituted.

In one embodiment of the invention, Q contains at least one substituent which is a reactive group that is attached to the heterocyclic (heteroaryl) ring (Q) by a covalent linkage. In one embodiment the compounds of the present invention which contain a reactive group label a wide variety of organic or inorganic substances that contain or are modified to contain functional groups with suitable reactivity, resulting in chemical attachment of the compounds of the present invention to form a conjugated substance.

As used herein, "reactive group" means a moiety on a compound of the present invention or that can be added to a compound of the present invention that is capable of chemically reacting with a functional group on a different compound to form a covalent linkage, or a moiety on a different compound that is capable of chemically reacting with a functional group on compound of the present invention to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the compound of the present invention and the substance to be conjugated results in one or more atoms of the reactive group to be incorporated into a new linkage attaching the dye to the conjugated substance.

One aspect of the invention is a PML of the formula (14), wherein Q is selected from a group consisting of carboxyl functionalized nitrogen containing heterocyclic ring (heteroaryl substituted with carboxyl). In this embodiment, heterocyclic ring and heteroaryl ring refers to heteroaryl ring as defined herein, such as pyridine and functionalized refers to substituted.

In one aspect of the invention PML is of the formula (14), wherein Q is selected from a group consisting of carboxyl functionalized nitrogen containing 6-membered heterocyclic ring (heteroaryl substituted with carboxyl), such as pyridine, pyrimidone, pyrazine, and pyridazine. (heteroaryl substituted with carboxyl). In this embodiment, heterocyclic ring and heteroaryl ring refers to heteroaryl ring as defined herein, such as pyridine and functionalized refers to substituted.

Another aspect of the invention is a PML of the formula (14), wherein Q is selected from a group consisting of carboxyl functionalized nitrogen containing 6-membered heterocyclic ring, (heteroaryl substituted with carboxyl), such as pyridine. (heteroaryl substituted with carboxyl). In this embodiment, heterocyclic ring and heteroaryl ring refers to heteroaryl ring as defined herein, such as pyridine and functionalized refers to substituted.

In another aspect of the invention PML is of the formula (14), wherein Q is selected from a group consisting of nicotinic acid and picolinic acid or a salt thereof.

In one aspect of the invention is a PML of the formula (14), wherein Q is selected from the groups shown:

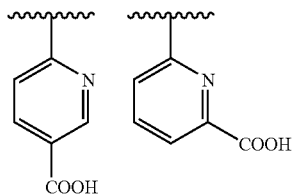

or a salt thereof.

In another aspect of the invention is a PML of the formula (14), wherein Q is selected from the groups shown:

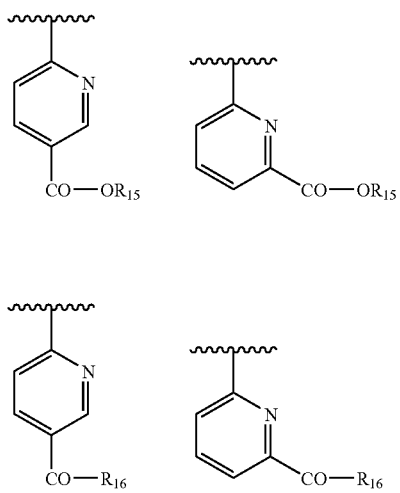

wherein, the carboxyl group is also in the form of an activated ester ($R_{15}$) or carbonyl halide ($R_{16}$=F, Cl, Br) that is capable of reacting with nucleophiles. The carboxyl group CO—$OR_{15}$ is also in a form selected from the group CO—Obenzotriazolyl, CO—ON-hydroxysuccinimidyl, CO—Otetrafluorophenyl, CO—Opentafluorophenyl, CO—Oimidazolyl, CO—Op-nitrophenyl.

The PML moiety typically originates from the coupling agent used in the synthesis of a compound of the present invention. For example, N,N'-diphenylformamidine and triethylorthoformate yields PML moieties. Malonaldehyde bis(phenylimine) hydrochloride, 1,1,3-trimethoxypropane, and 1,1,3,3-tetramethoxypropane and glutaconaldehyde dianil monocchloride also yield PML moieties (dyes).

In one aspect of the invention, the PML moiety is introduced into the dye using the malonodialdehydes moieties shown below:

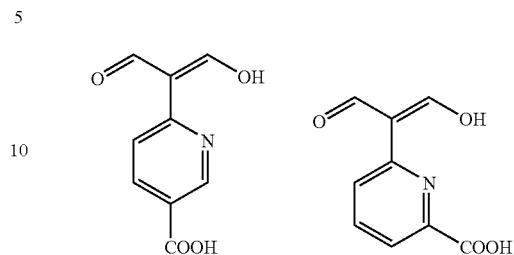

Accordingly, the present invention provides compounds representing $Z^1$-(PML)-$Z^2$ by the formula (2):

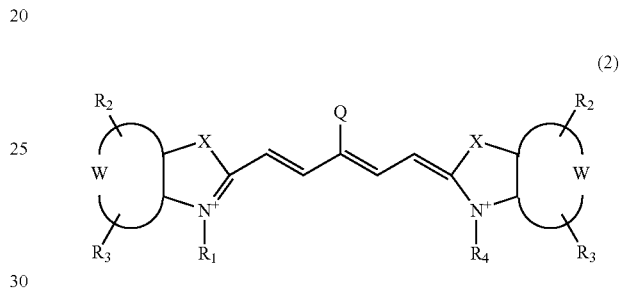

(2)

wherein $R_1$ is $(CH_2)_n SO_3^-$ or $(CH_2)_n SO_3H$.

In one aspect of the invention when Q is or contains an activated ester, the compound can be chemically linked to bifunctional linkers such as aminoethylmaleimide, aminopropylmaleimide, aminopropylazide, aminopropylthiol, mercaptoethylamine, propargylamine 3-aminopropanol, diaminopropane, and diaminobutane to provide additional reactive functional groups in a suitable solvent under neutral or basic conditions.

In one aspect of the invention when Q is or contains $NH_2$, the compound of the invention can be chemically linked to bifunctional linkers such as propargylic acid, succinimidylpyridinedithiopropionate, maleimide-PEG-N-hydroxysuccinimide ester to provide additional reactive functional groups in a suitable solvent under neutral or basic conditions.

When a compound of the invention is depicted herein by structure indicating the positions of the double bonds in the rings an polymethine linker, it is to be understood that the structure also encompasses any resonance structures as shown, for example, in the FIGURE below:

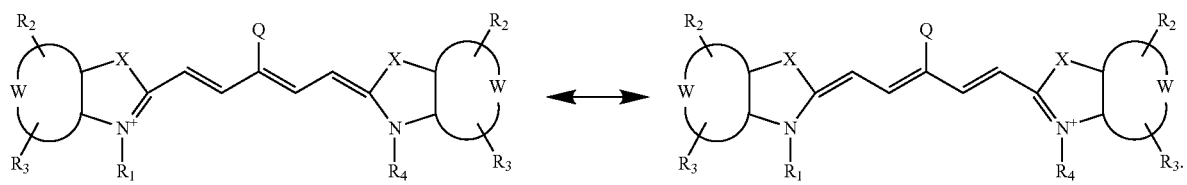

In one aspect, F is represented by formula (3):

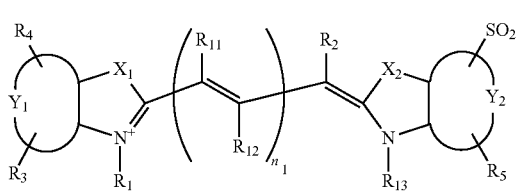

or a salt thereof, wherein:
- $X_1$, $X_2$ are independently selected from the group $C(CH_2K_1)(CH_2K_2)$, O, S, Se;
- $K_1$ and $K_2$ are independently selected from H and $C_1$-$C_{20}$ alkyl that is linear or branched, saturated or unsaturated, optionally containing N, S, O in various forms; or independently wherein $K_1$ and $K_2$ together are part of a cyclic ring optionally further substituted;
- $Y_1$, $Y_2$ are nonmetal atoms required to form a benzo-condensed ring or a naphtha-condensed ring or a pyrido-condensed ring;
- $n_1$ is 1, 2, or 3;
- $R_2$, $R_{11}$ and $R_{12}$ are independently H, F, Br, Cl, $C_1$-$C_6$ alkyl, $C_1$-$C_6$ alkoxy, aryloxy, a nitrogen heterocycle, a sulfonate, an iminium ion, or any two adjacent $R_{12}$ or $R_{11}$ substituents or $R_2$ and $R_{11}$ or $R_{12}$ substituents, when taken in combination, forms a 4-, 5-, or 6-membered saturated or unsaturated hydrocarbon ring that is optionally substituted one or more times by $C_1$-$C_6$ alkyl, halogen, or O or S-bearing moiety;
- $R_1$ and $R_{13}$ are selected from the group consisting of $(CH_2)_nCH_3$, $(CH_2)_nSO_3^-$ and $(CH_2)_nSO_3H$, wherein n is an integer selected from 0 to 6 when $R_1$ or $R_{13}$ is $(CH_2)_nCH_3$, and n is an integer selected from 2 to 6 when $R_1$ or $R_{13}$ is $(CH_2)_nSO_3^-$ or $(CH_2)_nSO_3H$;
- $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;
- $R_6$ is independently selected from $C_1$-$C_{20}$ alkyl that is linear or branched, saturated or unsaturated, aryl, alkylaryl, optionally containing halogens, N, S, O in various forms;
- $R_7$ is independently selected from H, $C_1$-$C_{20}$ alkyl that is linear or branched, saturated or unsaturated, aryl, alkylaryl, optionally containing halogens, N, S, O in various forms;
- $R_6$ and $R_7$, when taken in combination, forms a 4-, 5-, 6- or 7-membered saturated or unsaturated hydrocarbon ring optionally containing halogens, N, S, O in various forms.
- Q is absent; or Q is $C_1$-$C_6$ alkyl; or Q is $C_1$-$C_6$ cycloalkyl, wherein the alkyl or cyclic group contains 0-2 hetero atoms selected from N, O, S. The cyclic group may incorporate $NR_6$ and $CHR_7$ as a part of the ring system; or Q is carbonyl (CO) and $R_6$ is independently selected from H, $C_1$-$C_{20}$ alkyl that is linear or branched, saturated or unsaturated, aryl, alkylaryl, optionally containing halogens, N, S, O in various forms;
- W is either absent or is a group selected from $-SO_2NR_6$-Q-$CHR_7-$, $-O-$, $-COO-$, and $-CONH-$;
- h=0-70; k=0 or 1; d=0-12; m=0-12; p=0-12;
- Z is, or contains a N, O or S nucleophile functionality or is, or contains a functionality capable of reacting with N, O or S nucleophiles.

In one aspect, F is represented by formula (3):

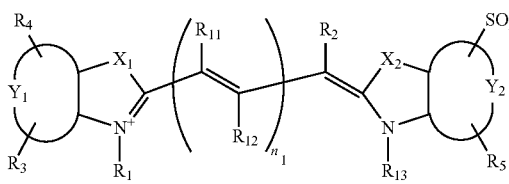

or a salt thereof, wherein:
- $X_1$, $X_2$ are independently selected from the group $C(CH_2K_1)(CH_2K_2)$, O, S, Se;
- $K_1$ and $K_2$ are independently selected from H and $C_1$-$C_{20}$ alkyl that is linear or branched, saturated or unsaturated, optionally containing N, S, O in various forms; or independently wherein $K_1$ and $K_2$ together are part of a cyclic ring optionally further substituted;
- $Y_1$, $Y_2$ are nonmetal atoms required to form a benzo-condensed ring or a naphtha-condensed ring or a pyrido-condensed ring;
- $n_1$ is 1, 2, or 3;
- $R_2$, $R_{11}$ and $R_{12}$ are independently H, F, Br, Cl, $C_1$-$C_6$ alkyl, $C_1$-$C_6$ alkoxy, aryloxy, a nitrogen heterocycle, a sulfonate, an iminium ion, or any two adjacent $R_{12}$ or $R_{11}$ substituents or $R_2$ and $R_{11}$ substituents, when taken in combination, forms a 4-, 5-, or 6-membered saturated or unsaturated hydrocarbon ring that is optionally substituted one or more times by $C_1$-$C_6$ alkyl, halogen, or O or S-bearing moiety;
- $R_1$ and $R_{13}$ are selected from the group consisting of H, $(CH_2)_nCH_3$, $(CH_2)_nSO_3^-$ and $(CH_2)_nSO_3H$, wherein n is an integer selected from 0 to 6 when $R_1$ or $R_{13}$ is $(CH_2)_nCH_3$, and n is an integer selected from 2 to 6 when $R_1$ or $R_{13}$ is $(CH_2)_nSO_3^-$ or $(CH_2)_nSO_3H$;
- $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;
- $R_6$ is independently selected from $C_1$-$C_{20}$ alkyl that is linear or branched, saturated or unsaturated, aryl, alkylaryl, optionally containing halogens, N, S, O in various forms;

$R_7$ is independently selected from H, $C_1$-$C_{20}$ alkyl that is linear or branched, saturated or unsaturated, aryl, alkylaryl, optionally containing halogens, N, S, O in various forms;

$R_6$ and $R_7$, when taken in combination, forms a 4-, 5-, 6- or 7-membered saturated or unsaturated hydrocarbon ring optionally containing halogens, N, S, O in various forms.

Q is absent; or Q is $C_1$-$C_6$ alkyl; or Q is $C_1$-$C_6$ cycloalkyl, wherein the alkyl or cyclic group contains 0-2 hetero atoms selected from N, O, S. The cyclic group may incorporate $NR_6$ and $CHR_7$ as a part of the ring system; or Q is carbonyl (CO) and $R_6$ is independently selected from H, $C_1$-$C_{20}$ alkyl that is linear or branched, saturated or unsaturated, aryl, alkylaryl, optionally containing halogens, N, S, O in various forms;

W is either absent or is a group selected from —$SO_2NR_6$-Q-$CHR_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles.

In certain embodiments, when F is formula (3) T is attached to the variable Z.

Compounds of the general formula (3) are described in PCT Application Titled: Biocompatible N,N-Disubstituted Sulfonamide-Containing Fluorescent Dye Labels, by Narayanan, Narasimhachari et al., filed Sep. 1, 2006, the entire contents of which are incorporated herein by reference.

Thus, in one aspect, the fluorophores (F) of the present invention are further substituted one or more times by sulfo or sulfoalkyl. By "sulfo" is meant sulfonic acid, or salt of sulfonic acid (sulfonate). Similarly, by "carboxyl" is meant carboxylic acid, carboxylate ester or salt of carboxylic acid. "Phosphate" is an ester of phosphoric acid, and includes salts of phosphate. "Phosphonate" means phosphonic acid and includes salts of phosphonate. Similarly for "carbonyl" groups such as, but not limited to carbonyl halode, (e.g., chloride) and carboxamide are included. As used herein, unless otherwise specified, the alkyl portions of substituents such as alkyl, alkoxy, arylalkyl, alkylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfo, amino, or hydroxy.

In one embodiment, the present invention is directed to fluorophores (F) represent by formula (3):

$Y_1, Y_2$ are nonmetal atoms required to form a benzo-condensed ring or a naphtha-condensed ring or a pyrido-condensed ring.

In one embodiment $Y_1, Y_2$ represent the atoms necessary to form one to two fused aromatic rings having 6 atoms in each ring, which atoms are selected from —CH, —C, $CR_8$, and —$NR_9$, where $R_9$ is 0 or 1 (such that each ring nitrogen is either quaternized or not), and each $R_8$ independently contains sulfo, trifluoromethyl, or halogen; $R_9$ independently contains a $C_1$-$C_8$ alkyl, in turn containing independently an H, amino or sulfo.

Incorporation of one or more non-hydrogen substituents on the fused rings can be used to tune the absorption and emission spectrum of the resulting dye.

Selected examples of the basic structure of $Z^1$ in formula (3) are shown below. These basic structures are optionally further substituted.

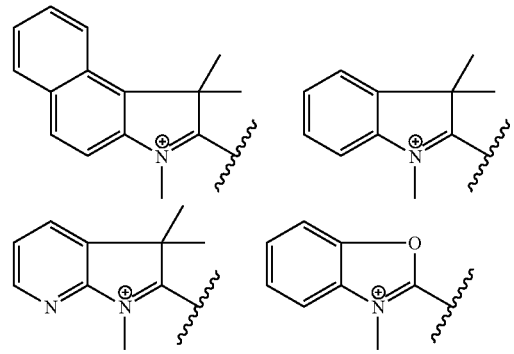

In one embodiment in formula (3) $X_1, X_2$ are independently selected from $C(CH_2K_1)(CH_2K_2)$, O, S, Se, wherein $K_1$ and $K_2$ are independently selected from H and $C_1$-$C_{20}$ alkyl that is linear or branched, saturated or unsaturated, optionally containing N, S, O in various forms; or independently wherein $K_1$ and $K_2$ together are part of a cyclic ring or X is independently selected from —$CR_{20}R_{21}$, wherein $R_{20}$ and $R_{21}$, which may be the same or different, are alkyl, cycloalkyl, or arylalkyl, together part of a cyclic system and optionally further substituted.

In one aspect of the invention, for compounds represented by formula (3) $R_3$ and $R_4$ taken in combination complete a five or six-membered ring.

In one embodiment in compounds represented by formula (3) $R_1$ and $R_{13}$ are selected from the group consisting of H, $(CH_2)_nCH_3$, $(CH_2)_nSO_3$— and $(CH_2)_nSO_3H$, wherein n is an integer selected from 0 to 6 when $R_1$ or $R_{13}$ is $(CH_2)_nCH_3$, and n is an integer selected from 2 to 6 when $R_1$ or $R_{13}$ is $(CH_2)_nSO_3$— or $(CH_2)_nSO_3H$. In one aspect of the invention $R_1$ and $R_{13}$ are substituents containing an aryl sulfonate or an amino group or a phthalimido group.

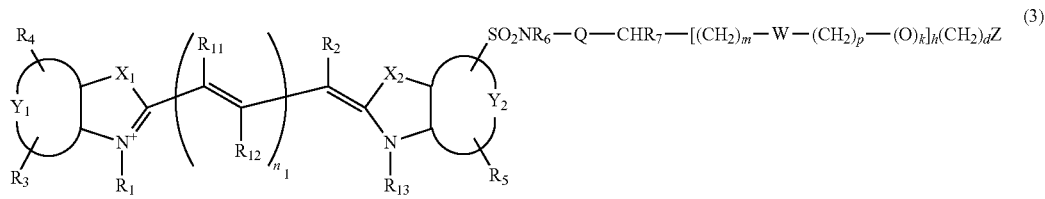

(3)

or a salt thereof, wherein:

In one embodiment in compounds represented by formula (3) $R_1$ and $R_{13}$ are selected from the group consisting of $(CH_2)_nCH_3$, $(CH_2)_nSO_3$— and $(CH_2)_nSO_3H$, wherein n is an integer selected from 0 to 6 when $R_1$ or $R_{13}$ is $(CH_2)_nCH_3$, and n is an integer selected from 2 to 6 when $R_1$ or $R_{13}$ is $(CH_2)_nSO_3$— or $(CH_2)_nSO_3H$. In one aspect of the invention $R_1$ and $R_{13}$ are substituents containing an aryl sulfonate or an amino group or a phthalimido group.

The substituents $R_3$, $R_4$ and $R_5$ in compounds represented by formula (3) are independently selected from the group H, halogens, carboxylate, carboxylic acid, carboxylic esters, amino, amide, alkyl or aryl sulfonamide, hydroxy, alkoxy, aryloxy, sulfate, cyano, nitro, azido, alkylamino, dialkylamino, trialkylammonium, phosphate, phosphate ester, phosphonate, sulphonic acid and a sulphonate moiety.

In one embodiment, the compounds of the present invention are sulfonated one or more times. If the compound of the present invention is substituted by sulfo (that is, for example, a sulfonic acid moiety, sulfonate moiety or sulfonamamide), it is typically sulfonated at $R_3$ or $R_4$ or $R_5$ or all, or sulfoalkylated independently at each $R_1$ or $R_{13}$ or both (that is, for example, $(CH_2)_nSO_3^-$ or $(CH_2)_nSO_3H$), or is both sulfonated and sulfoalkylated.

As used herein the terms sulfonic acid and $(CH_2)_nSO_3H$ or a sulfonate group and $(CH_2)_nSO_3^-$ can be used interchangeably. However in certain embodiments the terms a sulfonic acid moiety, sulfonate moiety or sulfonamamide refer to substituents which are attached to the remainder of the molecule by the a sulfonic acid moiety, sulfonate moiety or sulfonamamide moiety, i.e., —SO2NR'R".

In certain embodiment the present invention is directed to compounds as described herein where F is represented by structural formula (2):

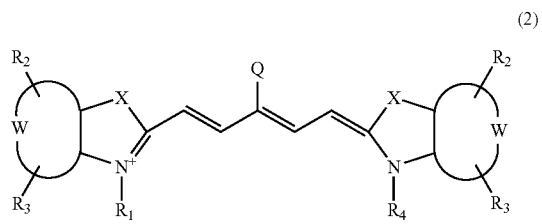

(2)

or a salt thereof, wherein:

X is independently selected from the group consisting of $C(CH_2Y_1)(CH_2Y_2)$, O, S, and Se;

$Y_1$ and $Y_2$ are independently selected from the group consisting of H, $C_1$-$C_{20}$ aliphatic group and a $C_1$-$C_{20}$ aliphatic group substituted with —OR*, N(R*)$_2$ or —SR*;

W represents a benzo-condensed, a naphtho-condensed or a pyrido-condensed ring;

$R_1$ is selected from the group consisting of H, $(CH_2)_xCH_3$, $(CH_2)_nSO_3^-$ and $(CH_2)_nSO_3H$, wherein x is an integer selected from 0 to 6 and n is an integer selected from 2 to 6;

$R_4$ is selected from the group consisting of H, $(CH_2)_xCH_3$, $(CH_2)_nSO_3^-$ and $(CH_2)_nSO_3H$, wherein x is an integer selected from 0 to 6 and n is an integer selected from 2 to 6;

$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from a group consisting of a heteroaryl ring substituted with a carboxyl group or 6-membered heteroaryl ring substituted with a carbonyl group.

In one embodiment, for compounds of formula (2):

a) the carboxyl substituent on Q is selected from the group consisting of an ester, an activated ester; or b) the carboxyl substituent on Q is selected from the group consisting of CO—Obenzotriazolyl, CO—ON-succinimidyl, CO—Otetrafluorophenyl, CO—Opentafluorophenyl, CO—Oimidazolyl, and CO—Op-nitrophenyl; and c) the carbonyl substituent on Q is in the form of a carbonyl halide.

In another embodiment, for compounds of formula (2): Q is a carboxyl substituted nitrogen containing heterocyclic ring.

In another embodiment, for compounds of formula (2): Q is selected from the group consisting of carboxyl substituted pyridine, pyrimidone, pyrazine, and pyridazine.

In another embodiment, for compounds of formula (2): Q is carboxyl substituted pyridine.

In another embodiment, for compounds of formula (2): Q is selected from a group consisting of isonicotinic acid, nicotinic acid and picolinic acid.

In another embodiment, for compounds of formula (2): Q is represented by a structural formula selected from a group consisting of:

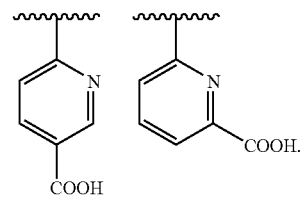

In another embodiment, for compounds of formula (2): Q is a carbonyl substituted nitrogen containing 6-membered heterocyclic ring In another embodiment, for compounds of formula (2): Q is a carbonyl substituted pyridine.

In another embodiment, for compounds of formula (2): at least one of the moieties $R_1$ to $R_3$ is, or contains a sulphonic acid moiety or a sulphonate moiety.

In another embodiment, for compounds of formula (2): $R_1$ and $R_4$ are independently $(CH_2)_nSO_3^-$ or $(CH_2)_nSO_3H$.

In another embodiment, for compounds of the present invention F is represented by a structural formula selected from:

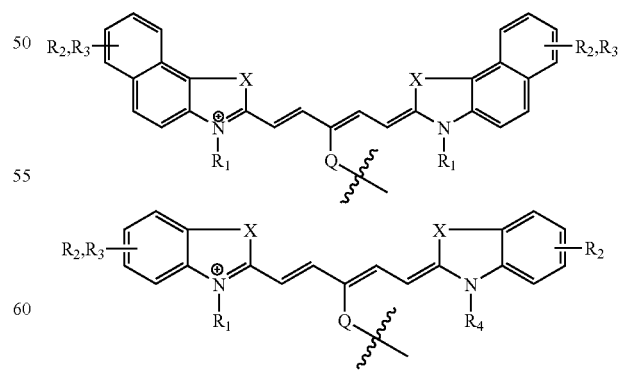

In another embodiment, for compounds of the present invention F is represented by a structural formula selected from:

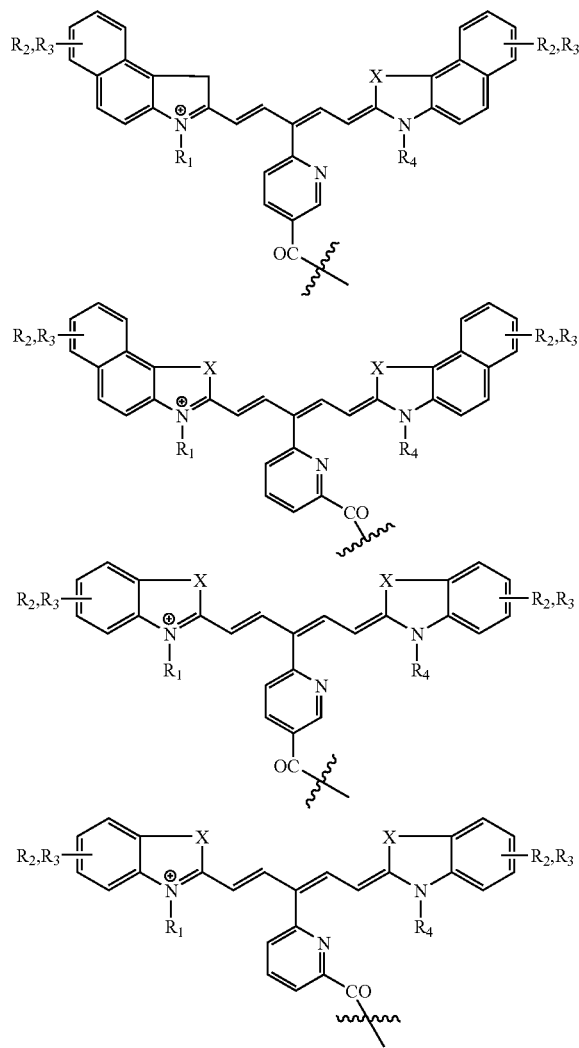

In another embodiment, for compounds of the present invention F is represented by structural formula (3):

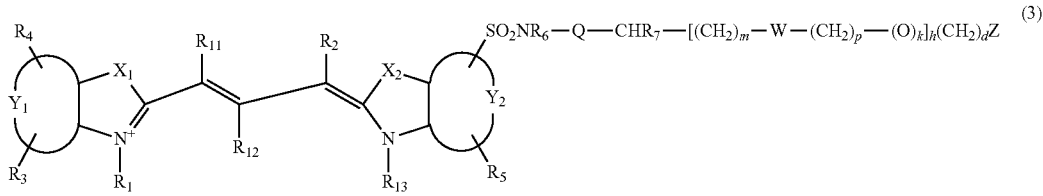

or a salt thereof, wherein:

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$, and $R_{12}$ are independently H, halogen, alkyl, alkoxy, aryloxy, aryl, a sulfonate, a group containing $SO_2NR_6$-Q-CHR$_7$—(CH$_2$)$_m$; i is 0 or 1; and m=0-12, an iminium ion, S-aryl, S-alkyl, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are —H, (CH$_2$)$_x$CH$_3$, when x is an integer selected from 0 to 6; or $R_1$ and $R_{13}$ are independently (CH$_2$)$_n$SO$_3^-$ or (CH$_2$)$_n$SO$_3$H when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or $R_6$ and $R_7$, taken together form a 4-, 5-, 6- or 7-membered heterocyclic or non-aromatic heterocyclic ring optionally substituted with halogen, OR*, N(R*)$_2$ or SR*; or NR$_6$, Q and CHR$_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$-Q-CHR$_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In another embodiment, for compounds of the present invention represented by formula (3) Z is a nucleophile functionality selected from the group consisting of —NH$_2$, —OH, and —SH.

In another embodiment, for compounds of the present invention represented by formula (3) Z is a functionality capable of reacting with N, O, S nucleophiles selected from the group consisting of —COCl, —(CO)O(CO)R, —CONHNH$_2$, substituted and unsubstituted N-hydroxysuccinimido esters, nitro- or fluoro-phenol esters, —NCS, —CHO, —COCH$_2$I, phosphoramidite and maleimide group.

In another embodiment, for compounds of the present invention represented by formula (3) the nucleophile is selected from the group consisting of —COCl, —(CO)O(CO)R, —CONHNH$_2$, substituted and unsubstituted N-hydroxysuccinimido esters, —NCS, —CHO, —COCH$_2$I, phosphoramidite and maleimide group.

In another embodiment, for compounds of the present invention represented by formula (3) at least two of the groups $R_1$, $R_3$, $R_4$, $R_5$ or $R_{13}$ contain a sulfonic acid or a sulfonate group.

In another embodiment, for compounds of the present invention represented by formula (3) $R_3$, $R_4$ and $R_5$ are each independently a group of the formula —SO$_2$NR$_6$-Q-CHR$_7$—[(CH$_2$)$_m$—W—(CH$_2$)$_p$—(O)$_k$]$_h$—(CH$_2$)$_d$Z.

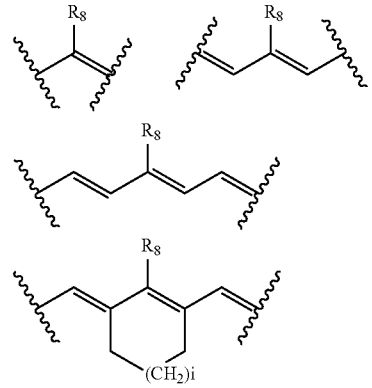

wherein $R_8$ is selected from the group consisting of H or Cl, Br or F.

In another embodiment, for compounds of the present invention F is represented by any one of formulae 4-6:

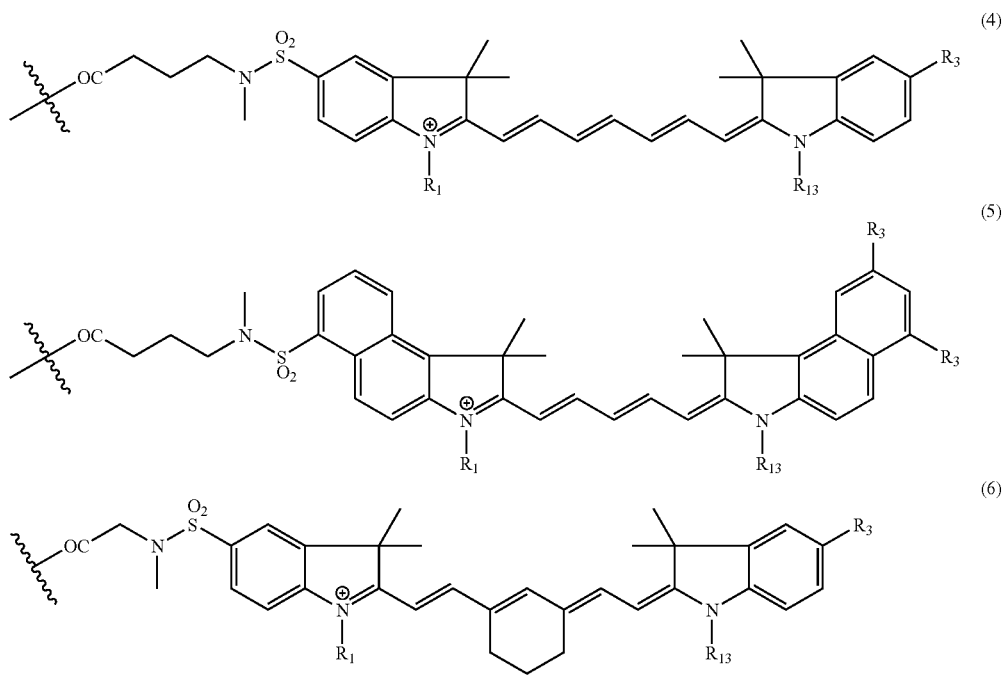

wherein:
$R_1$ and $R_{13}$ are independently selected from the group consisting of (CH$_2$)$_x$CH$_3$, (CH$_2$)$_n$SO$_3$— and (CH$_2$)$_n$SO$_3$H; wherein x is an integer selected from 0 to 6 and n is an integer selected from 2 to 6

$R_3$ is selected from the group consisting of H, carboxylate, carboxylic acid, carboxylic ester, amine, amide, sulfonamide, hydroxyl, alkoxyl, a sulphonic acid moiety and a sulphonate moiety.

In another embodiment, the compounds of the present invention are represented by the following structural formula:

T-F wherein: T contains one or more aromatic groups, as described above; and F is a fluorophore as described herein.

In another embodiment, for compounds of the present invention represented by formula (3) $R_3$, $R_4$ and $R_5$ is —SO$_2$NR$_6$-Q-CHR$_7$—[(CH$_2$)$_m$—W—(CH$_2$)$_p$—(O)$_k$]$_h$—(CH$_2$)$_d$Z.

In another embodiment, for compounds of the present invention represented by formula (3) $X_1$ and $X_2$ are both —C(CH$_3$)$_2$ In another embodiment, for compounds of the present invention represented by formula (3) —((C(R$_{11}$)═C(R$_{12}$))$_{n1}$—C(R$_2$)═ is represented by a structural formula selected from the group consisting of:

In another embodiment, for compounds of the present invention F is represented by structural formula (2):

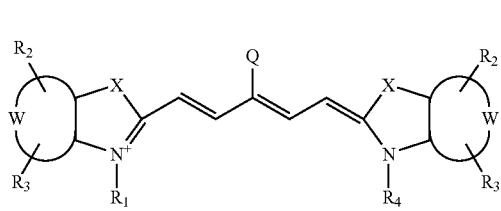

(2)

or a salt thereof, wherein:

X is independently selected from the group consisting of $C(CH_2Y_1)(CH_2Y_2)$, O, S, and Se;

$Y_1$ and $Y_2$ are independently selected from the group consisting of H, $C_1$-$C_{20}$ aliphatic group and a $C_1$-$C_{20}$ aliphatic group substituted with —OR*, $N(R^*)_2$ or —SR*;

W represents a benzo-condensed, a naphtho-condensed or a pyrido-condensed ring;

$R_1$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;

$R_4$ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;

$R_2$ and $R_3$ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from a group consisting of a heteroaryl ring substituted with a carboxyl group or 6-membered heteroaryl ring substituted with a carbonyl group.

Alternative variables for formula (2) are described above.

In another embodiment, for compounds of the present invention F is a fluorochrome represented by structural formula (3):

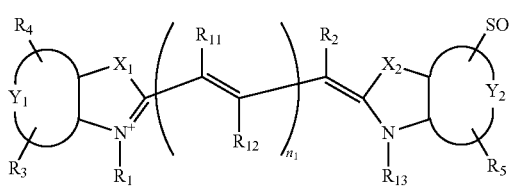

(3)

or a salt thereof, wherein:

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, $N(R^*)_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, F, Br, Cl, $C_1$-$C_6$ alkyl, $C_1$-$C_6$ alkoxy, aryloxy, a nitrogen-containing hetero cyclic ring, a nitrogen-containing heteroaromatic ring, a sulfonate, an iminium ion, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, $N(R^*)_2$ or SR*, when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, $N(R^*)_2$ or SR*; or $R_6$ and $R_7$, taken together form a 4-, 5-, 6- or 7-membered heterocyclic or non-aromatic heterocyclic ring optionally substituted with halogen, OR*, $N(R^*)_2$ or SR*; or $NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, $N(R^*)_2$ or —SR*; and W is absent or is a group selected from the group consisting of —$SO_2NR_6$-Q-$CHR_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

Alternative variables for formula (3) are as described above, in addition:

In one embodiment of the present invention for fluorophores represented by formula (3) Z is a nucleophile functionality selected from the group consisting of —$NH_2$, —OH, and —SH.

In one embodiment of the present invention for fluorophores represented by formula (3) Z is a functionality capable of reacting with N, O, S nucleophiles selected from the group consisting of —COCl, —(CO)O(CO)R, —CONHNH$_2$, substituted and unsubstituted N-hydroxysuccinimido esters, nitro- or fluoro-phenol esters, —NCS, —CHO, —COCH$_2$I, phosphoramidite and maleimide group.

In one embodiment of the present invention for fluorophores represented by formula (3) Q is absent.

In one embodiment of the present invention for fluorophores represented by formula (3) Q is C$_1$-C$_6$ alkyl;

In one embodiment of the present invention for fluorophores represented by formula (3) Q is C$_1$-C$_6$ substituted or unsubstituted or heterocyclic or non-aromatic heterocyclic ring system or NR$_6$, Q and CHR$_7$ taken together is a substituted or unsubstituted or heterocyclic or non-aromatic heterocyclic ring system.

In one embodiment of the present invention for fluorophores represented by formula (3) R$_3$, R$_4$ and R$_5$ are independently selected from the group consisting of H, carboxylate, carboxylic acid, carboxylic ester, amine, amide, sulfonamide, hydroxyl, alkoxyl, a sulphonic acid moiety, a sulphonate moiety and the moiety SO$_2$NR$_6$-Q-CHR$_7$—[(CH$_2$)$_m$—W—(CH$_2$)$_p$—(O)$_k$]$_h$(CH$_2$)$_d$Z;

In one embodiment the present invention is a compound represented by the following structural formula:

(T)$_2$-F wherein F is a fluorochrome represented by structural formula (3):

ring, wherein the carbocyclic rings are each independently optionally substituted one or more times by C$_1$-C$_6$ alkyl, halogen, or OR* or SR*;

R$_1$ and R$_{13}$ are (CH$_2$)$_x$CH$_3$, when x is an integer selected from 0 to 6; or R$_1$ and R$_{13}$ are independently (CH$_2$)$_n$SO$_3^-$ or (CH$_2$)$_n$SO$_3$H when n is an integer selected from 2 to 6;

wherein, R$_3$, R$_4$ and R$_5$ are independently selected from the group consisting of H, carboxylate, carboxylic acid, carboxylic ester, amine, amide, sulfonamide, hydroxyl, alkoxyl, a sulphonic acid moiety, a sulphonate moiety and the moiety SO$_2$NR$_6$-Q-CHR$_7$—[(CH$_2$)$_m$—W—(CH$_2$)$_p$—(O)$_k$]$_h$(CH$_2$)$_d$Z;

R$_6$ is selected from the group consisting of a substituted or unsubstituted C$_1$-C$_{20}$ aliphatic group, a substituted or unsubstituted aryl, a substituted or unsubstituted alkylaryl, wherein R$_6$ is optionally substituted with halogen, OR*, N(R*)$_2$ or SR*, when Q is absent, a carbonyl group, a substituted or unsubstituted C$_1$-C$_6$ alkyl group, wherein 0-2 of the methylene groups of the alkyl group are replaced by NH, O or S, or a substituted or unsubstituted C$_1$-C$_6$ carbocyclic, non-aromatic carbocyclic, heterocyclic or non-aromatic heterocyclic ring wherein the heterocyclic rings contains 1-2 heteroatoms; or R$_6$ is H, when Q is a carbonyl; and R$_7$ is selected from the group consisting of H, a substituted or unsubstituted C$_1$-C$_{20}$ aliphatic group, a substituted or

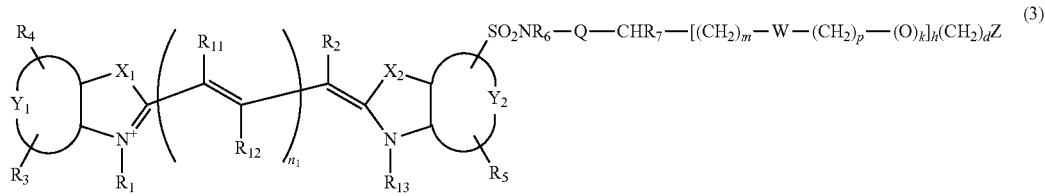

or a salt thereof, wherein:

X$_1$ and X$_2$ are independently selected from the group consisting of C(CH$_2$K$_1$)(CH$_2$K$_2$), O, S and Se;

K$_1$ and K$_2$ are independently selected from the group consisting of H, a C$_1$-C$_{20}$ aliphatic group and a C$_1$-C$_{20}$ aliphatic group substituted with —OR*, N(R*)$_2$ or —SR*; or K$_1$ and K$_2$ together are part of a substituted or unsubstituted carbocyclic, or heterocyclic ring;

Y$_1$ and Y$_2$ are each independently a benzo-condensed ring, a naphtha-condensed ring or a pyrido-condensed ring;

n$_1$ is 1, 2, or 3;

R$_2$, R$_{11}$ and R$_{12}$ are independently H, F, Br, Cl, C$_1$-C$_6$ alkyl, C$_1$-C$_6$ alkoxy, aryloxy, a nitrogen-containing heterocyclic ring, a nitrogen-containing heteroaromatic ring, a sulfonate, an iminium ion, or any two adjacent R$_{12}$ and R$_{11}$ substituents or R$_2$ and R$_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl unsubstituted aryl, a substituted or unsubstituted alkylaryl, wherein R$_7$ is optionally substituted with halogen, OR*, N(R*)$_2$ or SR*; or R$_6$ and R$_7$, taken together form a 4-, 5-, 6- or 7-membered heterocyclic or non-aromatic heterocyclic ring optionally substituted with halogen, OR*, N(R*)$_2$ or SR*; or NR$_6$, Q and CHR$_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$-Q-CHR$_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In one embodiment the present invention is directed to a fluorophore (F) represented by structural formula (3):

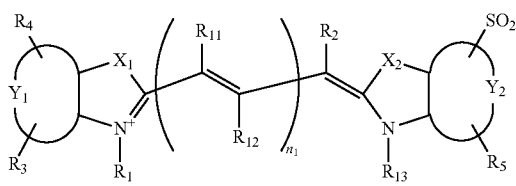

$SO_2NR_6-Q-CHR_7-[(CH_2)_m-W-(CH_2)_p-(O)_k]_h(CH_2)_dZ$ (3)

or a salt thereof.

$X_1$ and $X_2$ are independently selected from the group consisting of $C(CH_2K_1)(CH_2K_2)$, O, S and Se. In one embodiment $X_1$ and $X_2$ are independently $C(CH_2K_1)(CH_2K_2)$.

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic or heterocyclic ring. In one embodiment, $K_1$ and $K_2$ are independently H or a $C_1$-$C_{20}$ alkyl group. In one embodiment $K_1$ and $K_2$ are independently H or a $C_1$-$C_{10}$ alkyl group. In one embodiment $K_1$ and $K_2$ are independently H or a $C_1$-$C_{40}$ alkyl group.

$Y_1$ and $Y_2$ are each independently a benzo-condensed ring, a naphtha-condensed ring or a pyrido-condensed ring.

$n_1$ is 1, 2, or 3.

$R_2$, $R_{11}$ and $R_{12}$ are independently H, halogen, alkyl, alkoxy, aryloxy, aryl, a sulfonate, a group containing $SO_2NR_6$-Q-CHR$_7$—(CH$_2$)$_m$; i is 0 or 1; and m=0-12, an iminium ion, S-aryl, S-alkyl, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring. In one embodiment the carbocyclic rings are each independently optionally substituted one or more times by $C_1$-$C_6$ alkyl, halogen, or OR* or SR*. In one embodiment, $R_2$, $R_{11}$ and $R_{12}$ are independently H, alkyl, aryl, a sulfonate, a group containing $SO_2NR_6$-Q-CHR$_7$—(CH$_2$)$_m$; i is 0 or 1; and m=0-12, an iminium ion, S-aryl, S-alkyl, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*. In one embodiment, $R_2$, $R_{11}$ and $R_{12}$ are independently H, $C_{1-20}$ alkyl, a sulfonate, a group containing $SO_2NR_6$-Q-CHR$_7$—(CH$_2$)$_m$; i is 0 or 1; and m=0-12, or any two adjacent $R_{12}$ and $R_{11}$ substituents or $R_2$ and $R_{11}$ substituents, when taken in combination, form a 4-, 5-, or 6-membered carbocyclic ring, non-aromatic carbocyclic ring or carbocyclic aryl ring.

$R_1$ and $R_{13}$ are —H, (CH$_2$)$_x$CH$_3$, when x is an integer selected from 0 to 6; or $R_1$ and $R_{13}$ are independently (CH$_2$)$_n$SO$_3^-$ or (CH$_2$)$_n$SO$_3$H when n is an integer selected from 2 to 6.

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety. In one embodiment, $R_3$, $R_4$ and $R_5$ are independently selected from the group consisting of H, sulfonamide, a sulphonic acid moiety and a sulphonate moiety. In certain embodiments, $R_3$, $R_4$ and $R_5$ are independently, sulphonic acid or a salt thereof.

$R_6$ is selected from the group consisting of a substituted or unsubstituted $C_1$-$C_{20}$ aliphatic group, a substituted or unsubstituted aryl, a substituted or unsubstituted alkylaryl, when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms. In one embodiment $R_6$ is optionally substituted with halogen, OR*, N(R*)$_2$ or SR*. In another embodiment Q is optionally substituted with —OR*, N(R*)$_2$ or —SR*. In one embodiment $R_6$ is selected from the group consisting of a $C_1$-$C_{20}$ alkyl group, an aryl, an alkylaryl, when Q is absent, a carbonyl group a $C_1$-$C_6$ alkyl group, or a $C_1$-$C_6$ carbocyclic, non-aromatic carbocyclic, heterocyclic or non-aromatic heterocyclic ring. In one embodiment $R_6$ is a $C_1$-$C_{10}$ alkyl group, when Q is absent, a carbonyl group a $C_1$-$C_6$ alkyl group, or a $C_1$-$C_6$ carbocyclic, non-aromatic carbocyclic, heterocyclic or non-aromatic heterocyclic ring.

Alternatively $R_6$ is H, when Q is a carbonyl.

$R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*. In one embodiment $R_7$ is optionally substituted with halogen, OR*, N(R*)$_2$ or SR*. In one embodiment $R_7$ is selected from the group consisting of H, a $C_1$-$C_{20}$ alkyl group, an aryl, an alkylaryl. In one embodiment $R_7$ is selected from the group consisting of H, or a $C_1$-$C_{10}$ alkyl group.

Alternatively, $R_6$ and $R_7$, taken together form a 4-, 5-, 6- or 7-membered heterocyclic or non-aromatic heterocyclic ring. In one embodiment the carbocyclic, heterocyclic, non-aromatic carbocyclic or aryl ring is optionally substituted with halogen, OR*, N(R*)$_2$ or SR*. In one embodiment, $R_6$ and $R_7$, when taken in combination, form a 4-, 5-, 6- or 7-membered carbocyclic, heterocyclic, non-aromatic carbocyclic or aryl ring.

Alternatively, NR$_6$, Q and CHR$_7$ together form a substituted or unsubstituted or heterocyclic or non-aromatic heterocyclic ring system wherein the rings contain 1 or 2 heteroatoms. In one embodiment the carbocyclic, heterocyclic, non-aromatic carbocyclic or aryl ring is optionally substituted with halogen, OR*, N(R*)$_2$ or SR*. In one embodiment, $R_6$ and $R_7$, when taken in combination, form a 4-, 5-, 6- or 7-membered carbocyclic, heterocyclic, non-aromatic carbocyclic or aryl ring.

W is absent or is a group selected from the group consisting of —SO$_2$NR$_6$-Q-CHR$_7$—, —O—, —COO—, and —CONH—. In one embodiment, W is absent.

h=0-70; k=0 or 1; d=0-12; m=0-12; p=0-12. In one embodiment h=0-10; k=0 or 1; d=0-6; m=0-6; p=0-6.

Z is, or contains a N, O or S nucleophile functionality or is, or contains a functionality capable of reacting with N, O or S nucleophiles; and each R* is independently —H or C1-20 alkyl. In one embodiment each R* is independently —H or C1-10 alkyl.

In one embodiment, for compounds represented by formula (3):

$R_1$ and $R_{13}$ are —H; and the group —$((C(R_{11})=C(R_{12}))_{n1}$—$C(R_2)=$ is represented by a structural formula selected from the group consisting of:

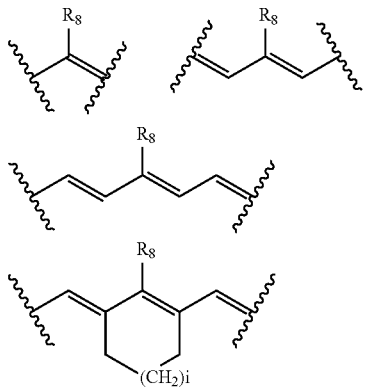

wherein $R_8$ is selected from the group consisting of H, a halogen atom, S-aryl, S-alkyl, alkyl, aryl, alkoxy, aryloxy and a group containing $SO_2NR_6$-Q-$CHR_7$—$(CH_2)_m$; i is 0 or 1; and m=0-12; and the remainder of the variables are as described above.

In certain embodiments for compounds represented by formula (2) Z is a nucleophile functionality selected from the group consisting of —$NH_2$, —OH, and —SH, and the remainder of the variables are as described above.

In certain other embodiment for compounds represented by formula (2) Z is a functionality capable of reacting with N, O, S nucleophiles selected from the group consisting of —COCl, —(CO)O(CO)R, —$CONHNH_2$, substituted and unsubstituted N-hydroxysuccinimido esters, nitro- or fluorophenol esters, —NCS, —CHO, —$COCH_2I$, phosphoramidite and maleimide group, and the remainder of the variables are as described above. In one embodiment the nucleophile is selected from the group consisting of —COCl, —(CO)O(CO)R, —$CONHNH_2$, substituted and unsubstituted N-hydroxysuccinimido esters, —NCS, —CHO, —$COCH_2I$, phosphoramidite and maleimide group.

In another embodiment the present invention is directed to a fluorophore (F) represented by structural formula (3):

clic, or heterocyclic ring. In one embodiment, $K_1$ and $K_2$ are independently H or a $C_1$-$C_{20}$ alkyl group. In one embodiment $K_1$ and $K_2$ are independently H or a $C_1$-$C_{10}$ alkyl group. In one embodiment $K_1$ and $K_2$ are independently H or a $C_1$-$C_{40}$ alkyl group.

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, F, Br, Cl, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring. In one embodiment the carbocyclic rings are each independently optionally substituted one or more times by $C_1$-$C_6$ alkyl, halogen, or OR* or SR*. In one embodiment, $R_2$, $R_{11}$ and $R_{12}$ are independently H, $C_1$-$C_6$ alkyl, a nitrogen-containing heterocyclic ring, a nitrogen-containing heteroaromatic ring, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*. In one embodiment, $R_2$, $R_{11}$ and $R_{12}$ are independently H, $C_{1-6}$ alkyl, a nitrogen-containing heterocyclic ring, or any two adjacent $R_{12}$ and $R_{11}$ substituents or $R_2$ and $R_{11}$ substituents, when taken in combination, form a 4-, 5-, or 6-membered carbocyclic ring, non-aromatic carbocyclic ring or carbocyclic aryl ring.

$R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety. In one embodiment, $R_3$, $R_4$ and $R_5$ are independently selected from the group consisting of H, sulfonamide, a sulphonic acid moiety and a sulphonate moiety. In certain embodiments, $R_3$, $R_4$ and $R_5$ are independently, sulphonic acid or a salt thereof.

$R_6$ is selected from the group consisting of a substituted or unsubstituted $C_1$-$C_{20}$ aliphatic group, a substituted or unsubstituted aryl, a substituted or unsubstituted alkylaryl, when Q

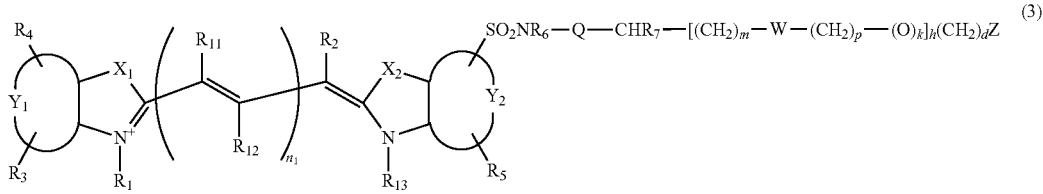

(3)

or a salt thereof.

$X_1$ and $X_2$ are independently selected from the group consisting of $C(CH_2K_1)(CH_2K_2)$, O, S and Se. In one embodiment $X_1$ and $X_2$ are independently $C(CH_2K_1)(CH_2K_2)$.

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyis absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms. In one embodiment $R_6$ is optionally substituted with halogen, OR*, N(R*)$_2$ or SR*. In another embodiment Q is optionally substituted with —OR*, N(R*)$_2$ or —SR*. In one embodiment R$_6$ is selected from the group consisting of a C$_1$-C$_{20}$ alkyl group, an aryl, an alkylaryl, when Q is absent, a carbonyl group a C$_1$-C$_6$ alkyl group, or a C$_1$-C$_6$ carbocyclic, non-aromatic carbocyclic, heterocyclic or non-aromatic heterocyclic ring. In one embodiment R$_6$ is a C$_1$-C$_{10}$ alkyl group, when Q is absent, a carbonyl group a C$_1$-C$_6$ alkyl group, or a C$_1$-C$_6$ carbocyclic, non-aromatic carbocyclic, heterocyclic or non-aromatic heterocyclic ring.

Alternatively R$_6$ is H, when Q is a carbonyl.

R$_7$ is selected from the group consisting of H, a substituted or unsubstituted C$_1$-C$_{20}$ aliphatic group, a substituted or unsubstituted aryl, a substituted or unsubstituted alkylaryl, wherein R$_7$ is optionally substituted with halogen, OR*, N(R*)$_2$ or SR*. In one embodiment R$_7$ is optionally substituted with halogen, OR*, N(R*)$_2$ or SR*. In one embodiment R$_7$ is selected from the group consisting of H, a C$_1$-C$_{20}$ alkyl group, an aryl, an alkylaryl. In one embodiment R$_7$ is selected from the group consisting of H, or a C$_1$-C$_{10}$ alkyl group; or Alternatively, R$_6$ and R$_7$, taken together form a 4-, 5-, 6- or 7-membered heterocyclic or non-aromatic heterocyclic ring. In one embodiment the carbocyclic, heterocyclic, non-aromatic carbocyclic or aryl ring is optionally substituted with halogen, OR*, N(R*)$_2$ or SR*. In one embodiment, R$_6$ and R$_7$, when taken in combination, form a 4-, 5-, 6- or 7-membered carbocyclic, heterocyclic, non-aromatic carbocyclic or aryl ring.

Alternatively, NR$_6$, Q and CHR$_7$ together form a substituted or unsubstituted or heterocyclic or non-aromatic heterocyclic ring system wherein the rings contain 1 or 2 heteroatoms. In one embodiment the carbocyclic, heterocyclic, non-aromatic carbocyclic or aryl ring is optionally substituted with halogen, OR*, N(R*)$_2$ or SR*. In one embodiment, R$_6$ and R$_7$, when taken in combination, form a 4-, 5-, 6- or 7-membered carbocyclic, heterocyclic, non-aromatic carbocyclic or aryl ring.

W is absent or is a group selected from the group consisting of —SO$_2$NR$_6$-Q-CHR$_7$—, —O—, —COO—, and —CONH—. In one embodiment, W is absent.

h=0-70; k=0 or 1; d=0-12; m=0-12; p=0-12. In one embodiment h=0-10; k=0 or 1; d=0-6; m=0-6; p=0-6.

Z is, or contains a N, O or S nucleophile functionality or is, or contains a functionality capable of reacting with N, O or S nucleophiles; and each R* is independently —H or C1-20 alkyl. In one embodiment each R* is independently —H or C1-10 alkyl.

In certain embodiments for compounds represented by formula (2) Z is a nucleophile functionality selected from the group consisting of —NH$_2$, —OH, and —SH, and the remainder of the variables are as described above.

In certain other embodiment for compounds represented by formula (2) Z is a functionality capable of reacting with N, O, S nucleophiles selected from the group consisting of —COCl, —(CO)O(CO)R, —CONHNH$_2$, substituted and unsubstituted N-hydroxysuccinimido esters, nitro- or fluorophenol esters, —NCS, —CHO, —COCH$_2$I, phosphoramidite and maleimide group, and the remainder of the variables are as described above. In one embodiment the nucleophile is selected from the group consisting of —COCl, —(CO)O(CO)R, —CONHNH$_2$, substituted and unsubstituted N-hydroxysuccinimido esters, —NCS, —CHO, —COCH$_2$I, phosphoramidite and maleimide group.

In one embodiment of the present invention, for compounds represented by formula (2) as described in the preceding thirty six paragraphs at least two of the groups R$_1$, R$_3$, R$_4$, R$_5$ or R$_{13}$ contain a sulfonic acid or a sulfonate group.

In one embodiment of the present invention, for compounds represented by formula (2) as described in the preceding thirty seven paragraphs R$_3$, R$_4$ and R$_5$ are each independently a group of the formula —SO$_2$NR$_6$-Q-CHR$_7$—[(CH$_2$)$_m$—W—(CH$_2$)$_p$—(O)$_k$]$_h$—(CH$_2$)$_d$Z.

In one embodiment of the present invention, for compounds represented by formula (2) as described in the preceding thirty eight paragraphs one of R$_3$, R$_4$ and R$_5$ is —SO$_2$NR$_6$-Q-CHR$_7$—[(CH$_2$)$_m$—W—(CH$_2$)$_p$—(O)$_k$]$_h$—(CH$_2$)$_d$Z.

In one embodiment of the present invention, for compounds represented by formula (2) as described in the preceding thirty nine paragraphs X$_1$ and X$_2$ are both —C(CH$_3$)$_2$ In one embodiment of the present invention, for compounds represented by formula (2) as described in the preceding forty paragraphs the group —((C(R$_{11}$)=C(R$_{12}$))$_{n1}$—C(R$_2$)= is represented by a structural formula selected from the group consisting of:

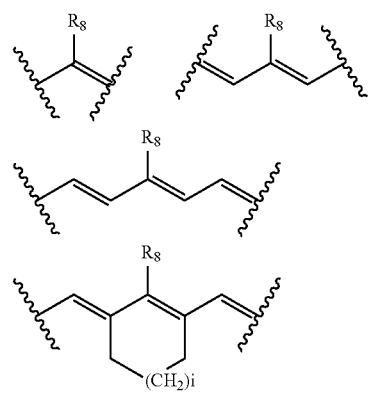

wherein R$_8$ is selected from the group consisting of H or Cl, Br or F

In one embodiment the present invention is directed to a compound represented by structural formula (3):

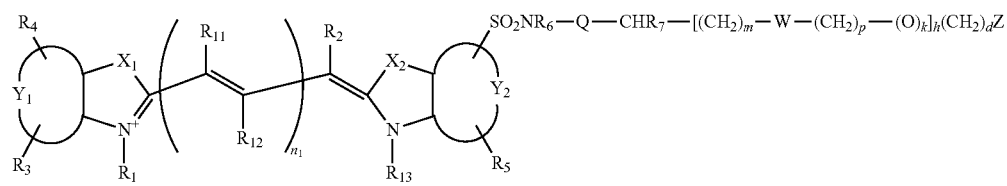

or a salt thereof, wherein:

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, halogen, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, a group containing $SO_2NR_6$-Q-$CHR_7$—$(CH_2)_m$; i is 0 or 1; and m=0-12 or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or

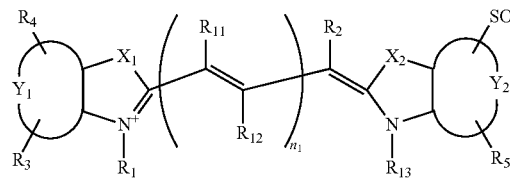

SR* when Q is absent, a carbonyl group a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic or heterocyclic ring wherein the ring may incorporate $NR_6$ and $CHR_7$ as a part of the ring system and the heterocyclic ring contains 0-2 heteroatoms, wherein Q is optionally substituted with —OR*, N(R*)$_2$ or —SR*; or $R_6$ is H, when Q is a carbonyl;

$R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*;

or $R_6$ and $R_7$, when taken in combination, form a 4-, 5-, 6- or 7-membered carbocyclic, heterocyclic, non-aromatic carbocyclic or aryl optionally substituted with halogen, OR*, N(R*)$_2$ or SR*;

W is absent or is a group selected from the group consisting of —$SO_2NR_6$-Q-$CHR_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In certain embodiments, the group —$((C(R_{11})=C(R_{12}))_{n1}$—$C(R_2)=$ is represented by a structural formula selected from the group consisting of:

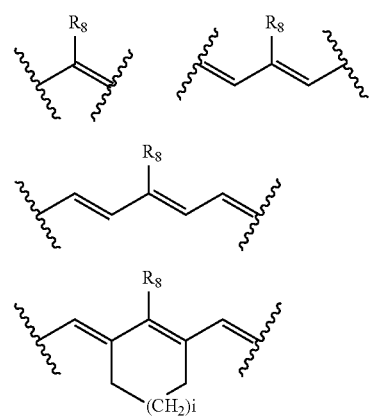

wherein $R_8$ is selected from the group consisting of H, a halogen atom, and a group containing $SO_2NR_6$-Q-$CHR_7$—$(CH_2)_m$; i is 0 or 1; and m=0-12, and the remainder of the variables are as described immediately above.

In one embodiment the present invention is directed to a compound represented by structural formula (3):

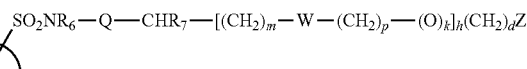

or a salt thereof, wherein:

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently a group containing $SO_2NR_6$-Q-$CHR_7$—$(CH_2)_m$; i is 0 or 1; and m=0-12, alkyl, aryl, alkoxy, halogen, S-aryl or S-alkyl, $R_1$ and $R_{13}$ are H;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or $R_6$ and $R_7$, taken together form a 4-, 5-, 6- or 7-membered heterocyclic or non-aromatic heterocyclic ring optionally substituted with halogen, OR*, N(R*)$_2$ or SR*; or $NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$-Q-CHR$_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In certain embodiments of the present invention $R_2$, $R_{11}$ and $R_{12}$ are independently, S-aryl or S-alkyl, and the remainder of the variables are as described immediately above.

Suitable examples of appropriate PML moieties for the compounds of the present invention (carbocyanine dyes) have been previously described in the literature, including PML moieties that incorporate nonhydrogen substituents, ring structures, and rigidizing elements (U.S. Pat. No. 5,831,098 to Ollmann, Jr (1998); U.S. Pat. No. 6,086,737 to Patonay et al. (2000); U.S. Pat. No. 6,048,982 to Waggoner (2000); and U.S. Pat. No. 5,453,505 to Lee et al. (1995); U.S. Pat. No. 5,639,874 to Middendorf et al. (1997); U.S. Pat. No. 3,864,644 to Lincoln et al (1975); U.S. Pat. No. 4,011,086 to Simson (1977); U.S. Pat. No. 6,747,159 to Caputo (2004); all incorporated by reference).

In one embodiment of the present invention a reactive group (or chemically linked molecule) can be attached to $Y_2$, in certain compounds (indocyanine dyes) of the present invention. In addition to a reactive group at $Y_2$, the compounds may be additionally sulfonated at least four times (at $R_3$ and $R_4$, and as sulfoalkyl at both $R_1$ and $R_{13}$). In one embodiment of the present invention a reactive group (or chemically linked molecule) can be attached to $Y_2$, in certain compounds (indocyanine dyes) of the present invention. In addition to a reactive group at $Y_2$, the compounds may be additionally sulfonated up to four times (at $R_3$ and $R_4$, and as sulfoalkyl at both $R_1$ and $R_{13}$). This extra sulfonation, results in reactive dyes and dye conjugates that have novel properties, such as, for example, improved aqueous solubility.

As used herein, "reactive group" means a moiety on a compound of the present invention or that can be added to a compound of the present invention that is capable of chemically reacting with a functional group on a different compound to form a covalent linkage, or a moiety on a different compound that is capable of chemically reacting with a functional group on compound of the present invention to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the compound of the present invention and the substance to be conjugated results in one or more atoms of the reactive group to be incorporated into a new linkage attaching the dye to the conjugated substance.

The PML moiety typically originates from the coupling agent used in the synthesis of the compounds (dye) of the present invention. For example, N,N'-diphenylformamidine and triethylorthoformate yields PML moieties. Malonaldehyde bis(phenylimine) hydrochloride, 1,1,3-trimethoxypropane, and 1,1,3,3-tetramethoxypropane and glutaconaldehyde dianil monochloride also yield dyes.

The choice of the PML, which is in effect the choice of $n_1$ and $R_2$, $R_{12}$, $R_{11}$ may also affect the absorption and fluorescence properties of the fluorochrome. The length of the PML between $Z^1$ and $Z^2$ also affects the absorption and fluorescence properties of the fluorochrome. Where $n_1$=1, and the indolium heterocycle is not fused to additional rings, the resulting fluorochromes typically exhibits an absorption maximum near 550 nm. Where $n_1$=2, the fluorochromes typically absorb maximally near 650 nm. The fluorochromes, where $n_1$=3, typically absorbs maximally near 750 nm.

In one aspect of the invention, $n_1$ is 1, 2, or 3; $R_2$, $R_{11}$ and $R_{12}$ are independently H, F, Br, Cl, $C_1$-$C_6$ alkyl, $C_1$-$C_6$ alkoxy, aryloxy, a nitrogen heterocycle, a sulfonate, an iminium ion, or any two adjacent $R_{12}$ or $R_{11}$ substituents or $R_2$ and $R_{11}$ substituents, when taken in combination, forms a 4-, 5-, or 6-membered saturated or unsaturated hydrocarbon ring that is optionally substituted one or more times by $C_1$-$C_6$ alkyl, halogen, or O or S-bearing moiety.

One aspect of the invention, the fluorophore (F) is represented by formula (3), wherein only one $R_{12}$ is selected from a group consisting of a functionalized nitrogen-containing heterocyclic ring (substituted nitrogen containing heteroaryl ring). In this embodiment, heterocyclic ring and heteroaryl ring refers to heteroaryl ring as defined herein, such as pyridine and functionalized refers to substituted.

Another aspect of the invention, the fluorophore (F) is represented by formula (3), wherein only one $R_{12}$ is selected from a group consisting of a pyridine ring.

In one aspect of the invention, the PML moiety is introduced into the dye using the malonodialdehyde moieties shown below:

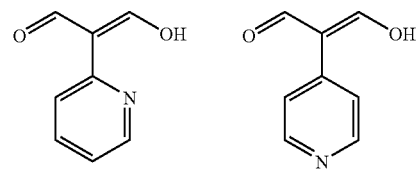

In one aspect of the invention the pyridine nitrogen, on the PML, can be quaternized to modify the physical and pharmacological properties of the compounds of the present invention.

The functional side arm can be introduced in either $Z^1$ or $Z^2$. The functional side arm is positioned anywhere in the moiety described by $Y_1$ or $Y_2$.

In one aspect of the invention, formula (3) is represented according to the following:

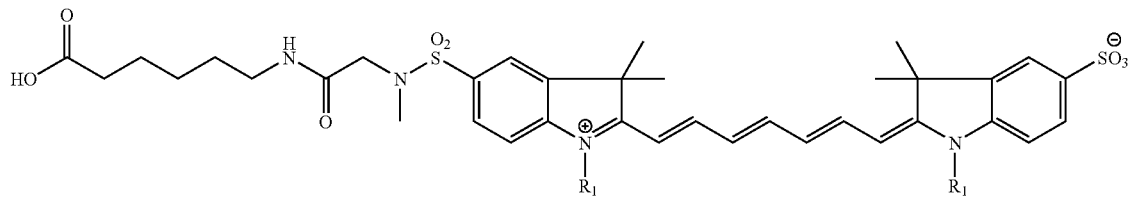

wherein each $R_1$ is independently selected from the group consisting of $(CH_2)_xCH_3$, $(CH_2)_nSO_3-$ and $(CH_2)_nSO_3H$; wherein x is an integer selected from 0 to 6 and n is an integer selected from 2 to 6.

The functional side arm is typically introduced by the reaction of an appropriately amine functionalized side arm to a sulfonyl chloride group on $Y_1$ or $Y_2$ of formula (3). The amine functionalized side arm may exist in the form of an amine salt.

In one embodiment the amine functional side arm used to couple to the sulfonyl chloride on $Y_1$ or $Y_2$ is a hydrochloride salt. Thus, $R_6$ is independently selected from $C_1$-$C_{20}$ alkyl that is linear or branched, saturated or unsaturated, aryl, alkylaryl, optionally containing halogens, N, S, O in various forms.

In one aspect of the invention $R_6$ is a methyl group. Thus, $R_7$ is independently selected from H, $C_1$-$C_{20}$ alkyl that is linear or branched, saturated or unsaturated, aryl, alkylaryl, optionally containing halogens, N, S, O in various forms.

In one aspect Q is absent. In another aspect Q is $C_1$-$C_6$ alkyl. In another embodiment Q is $C_1$-$C_6$ cycloalkyl, wherein the alkyl or cyclic group contains 0-2 hetero atoms selected from N, O, S. The cyclic group may incorporate $NR_6$ and $CHR_7$ as a part of the ring system. In a further aspect Q is carbonyl (CO) and $R_6$ is independently selected from H, $C_1$-$C_{20}$ alkyl that is linear or branched, saturated or unsaturated, aryl, alkylaryl, optionally containing halogens, N, S, O in various forms.

In one embodiment the moiety —$SO_2NR_6$-Q-$CHR_7$— is of formula:

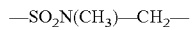

In another aspect of the invention, Q, $R_6$ and $R_7$, when taken in combination, forms a 4-, 5-, 6- or 7-membered saturated or unsaturated hydrocarbon ring optionally containing halogens, N, S, O in various forms.

In one embodiment the moiety —$SO_2NR_6$-Q-$CHR_7$— is of formula:

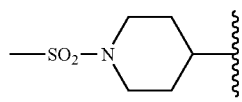

In one aspect of the invention, the moiety —$SO_2NR_6$-Q-$CHR_7$—, when m=0, p=0, k=0, h=0, and d=0, is prepared from cyclic-alpha-amino acids such as proline, hydroxyproline, 1,2,3,4-tetrahydroisoquinoline-3-carboxylic acid and the appropriate sulfonyl chloride.

In one aspect of the invention, the moiety —$SO_2NR_6$-Q-$CHR_7$— is of formula:

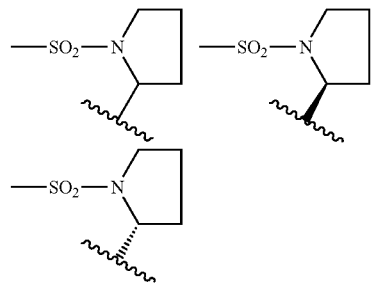

In one aspect of the invention, the moiety —$SO_2NR_6$-Q-$CHR_7$— is of formula:

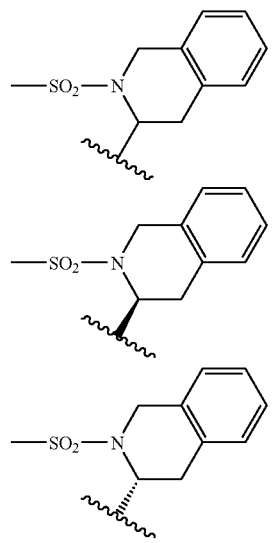

W is either absent or is a group selected from —$SO_2NR_6$-Q-$CHR_7$—, —O—, —COO—, and —CONH—.

In one aspect of the invention, the values of h=0-70; k=0 or 1; d=0-12; m=0-12; p=0-12.

In one aspect, Z is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. In another aspect of the invention, Z is a succinimidyl ester of a carboxylic acid, a maleimide, an iodoacetamide or a succinimidyl ester of a carboxylic acid. In a further aspect of the invention, Z is independently a nucleophile functionality selected from the group consisting of —NH$_2$, —OH, and —SH. Furthermore, Z can be a functionality capable of reacting with N, O, S nucleophiles including but not limited to the group consisting of —COCl, —(CO)O(CO)R, —CONHNH$_2$, substituted and unsubstituted N-hydroxysuccinimido esters, —NCS, —CHO, —COCH$_2$I, phosphoramidite and maleimide group.

In one aspect of the invention, Z=CO—OR$_{15}$ or Z=CO—R$_{16}$ and is in the form of an activated ester (R$_{15}$) or carbonyl halide (R$_{16}$=F, Cl, Br) that is capable of reacting with nucleophiles. The carboxyl group CO—OR$_{15}$ is also in a form selected from the group CO—Obenzotriazolyl, CO—ONhydroxysuccinimidyl, CO—Otetrafluorophenyl, CO—Opentafluorophenyl, CO—Oimidazolyl, CO—Op-nitrophenyl.

In one aspect of the invention, Z=CO—OR$_{15}$ or Z=CO—R$_{16}$ and is in the form of an activated ester (R$_{15}$) or carbonyl halide (R$_{16}$=F, Cl, Br) that is capable of reacting with nucleophiles. The carboxyl group CO—OR$_{15}$ is also in a form selected from the group CO—Obenzotriazolyl, CO—ONsuccinimidyl, CO—Otetrafluorophenyl, CO—Opentafluorophenyl, CO—Oimidazolyl, CO—Op-nitrophenyl.

In one aspect of the invention, Z is an azide. In another aspect of the invention Z is an alkyne.

In one aspect of the invention when Z is an activated ester, the compound can be chemically linked to bifunctional linkers such as aminoethylmaleimide, aminopropylmaleimide, aminopropylazide, aminopropylthiol, mercaptoethylamine, propargylamine 3-aminopropanol, diaminopropane, and diaminobutane to provide additional reactive functional groups in a suitable solvent under neutral or basic conditions.

In one aspect of the invention when Z is NH$_2$, the compound of the invention can be chemically linked to bifunctional linkers such as propargylic acid, succinimidylpyridinedithiopropionate, maleimide-PEG-N-hydroxysuccinimide ester to provide additional reactive functional groups in a suitable solvent under neutral or basic conditions.

In one aspect of the invention, formula (3) is represented according to the following, wherein at least two of the groups R$_1$, R$_3$, R$_4$, R$_5$ or R$_{13}$ contain a sulfonic acid or a sulfonate group.

In one aspect of the invention, formula (3) is represented according to the following, wherein R$_3$, R$_4$ and R$_5$ are independently all a group of the formula —SO$_2$NR$_6$-Q-CHR$_7$—[(CH$_2$)$_m$—W—(CH$_2$)$_p$—(O)$_k$]$_h$—(CH$_2$)$_d$Z.

In one aspect of the invention, formula (3) is represented according to the following, wherein X$_1$ and X$_2$ are both —C(CH$_3$)$_2$.

In one aspect of the invention, formula (3) is represented according to the following, wherein the polymethine linker having from 3 to 7 carbon atoms is selected from the group consisting of:

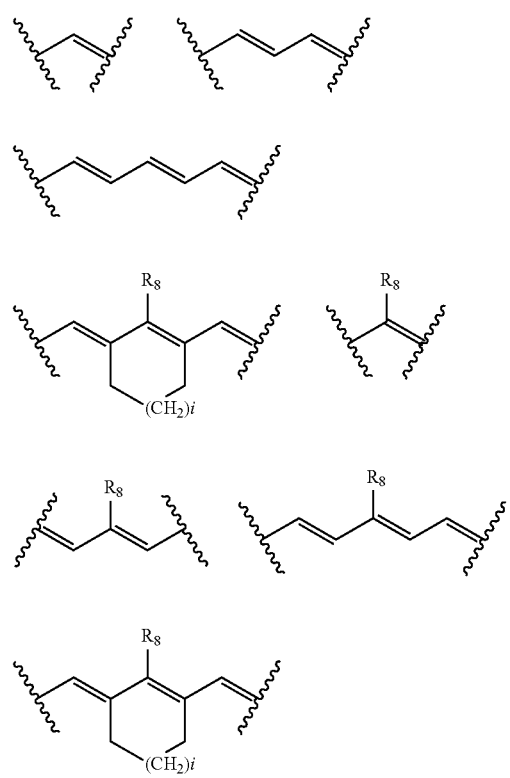

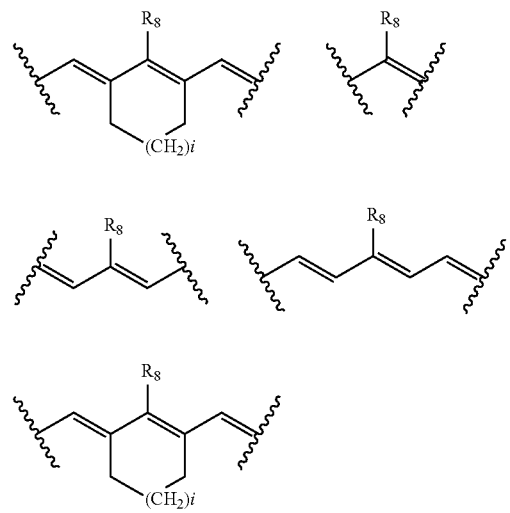

wherein R$_8$ is selected from the group consisting of H, a halogen atom, the group —S-aryl, S-alkyl, alkyl, aryl, alkoxy, aryloxy, and a group containing SO$_2$NR$_6$-Q-CHR$_7$—(CH$_2$)$_m$ and i is 0 or 1; m=0-12.

In one aspect of the invention, formula (3) is represented according to the following, wherein the polymethine linker having from 3 to 7 carbon atoms is selected from the group consisting of:

wherein R$_8$ is selected from the group consisting of H, a halogen atom, the group and a group containing SO$_2$NR$_6$-Q-CHR$_7$—(CH$_2$)$_m$ and i is 0 or 1; m=0-12.

In one aspect of the invention, formula (3) is represented according to the following:

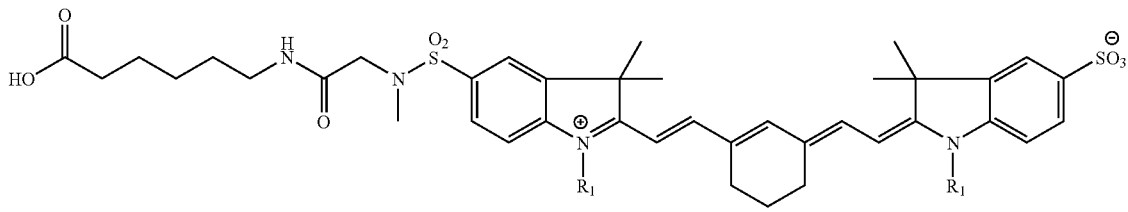

When a compound of the invention is depicted herein by structure indicating the positions of the double bonds in the rings an polymethine linker, it is to be understood that the structure also encompasses any resonance structures as shown, for example, in the FIGURE below:

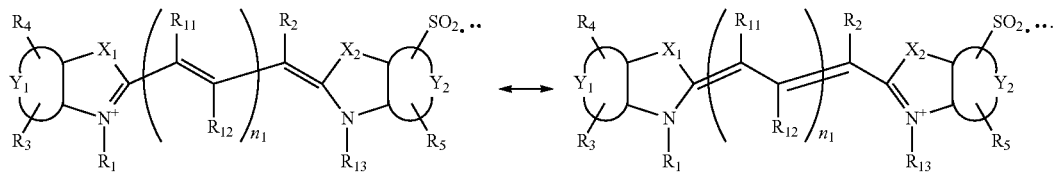

In certain embodiments of the present invention the when $R_6$ is other then hydrogen, unwanted sidechain reactions, are reduced, prevented or inhibited.

In one aspect the fluorophore is of the formula (1 a) or a salt thereof:

wherein, F is represented by formula (2) as described herein; F is represented by formula (3) as described herein, or F is represented by formula (3) and $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety, a sulphonate moiety and the moiety $SO_2NR_6$-Q-$CHR_7$—[$(CH_2)_m$—W—$(CH_2)_p$—$(O)_k]_h(CH_2)_qZ$, and the remainder of the variables are as described herein.

n is a positive integer from 1 to 5. In one embodiment n is 2. In one embodiment n is 4.

A "fluorophore" includes, but is not limited to, a fluorochrome, a non-fluorochrome fluorophore, a fluorescence quencher, an absorption fluorophore, a fluorophore, any organic or inorganic dye, metal chelate, or any fluorescent enzyme substrate, including protease activatable enzyme substrates.

A "biocompatible molecule" or "biomolecule" is a molecule that is compatible with a biological environment and to which one or more fluorophore molecules can be attached (chemically linked). Endogenous biomolecules include, but are not limited to, albumin, transferrin, fatty acid binding proteins, globulins, red blood cells, lymphocytes, stem cells or other cells, antibodies and lipoproteins.

"Attached" is meant connected by any attractive force between atoms strong enough to allow the combined aggregate to function as a unit. This includes, but is not limited to, covalent bonds, non-covalent bonds such as ionic bonds, metallic bonds, and bridge bonds, and hydrophobic interactions and van der Waals interactions.

In certain embodiments, the present invention is directed to compound (fluorophores) with excitation and emission wavelengths in the red and near infrared spectrum in the range 550-1300 or 400-1300 nm or about 440 and about 1100 nm, between about 550 and about 800 nm, between about 500 and about 900 nm or between about 600 and about 900 nm and conjugates thereof. Use of this portion of the electromagnetic spectrum maximizes tissue penetration and minimizes absorption by physiologically abundant absorbers such as hemoglobin (<650 nm) and water (>1200 nm). It will be appreciated that fluorochromes with excitation and emission wavelengths in other spectrums, such as the visible and ultraviolet light spectrum, can also be employed in the compounds (compositions) and methods of the present invention.

In certain embodiment the compounds (near infrared fluorophores) of the present invention which are suitable for in vivo use in general exhibit one or more of the following characteristics: (1) narrow spectral characteristics, (2) high sensitivity (quantum yield), (3) biocompatibility, and (4) decoupled absorption and excitation spectra.

It will be appreciated that the use of fluorophores with excitation and emission wavelengths in other spectrums, such as the visible and ultraviolet light spectrum, can also be employed in the compounds (compositions) and methods of the present invention.

Various near infrared fluorophores are commercially available and can be used in the compounds (probes or fluorophores, that is, compounds of the formula (1): T-F where F is the commercially available fluorophore) of the present invention. Exemplary fluorophores include the following: Cy5.5, Cy5 and Cy7 (Amersham, Arlington Hts., Ill.); IRD41 and IRD700 (LI-COR, Lincoln, Nebr.); NIR-1 and 1C5-OSu, (Dejindo, Kumamoto, Japan); Alexflour 660, Alexflour 680 (Molecular Probes, Eugene, Oreg.), LaJolla Blue (Diatron, Miami, Fla.); FAR-Blue, FAR-Green One, and FAR-Green Two (Innosense, Giacosa, Italy), ADS 790-NS and ADS 821-NS (American Dye Source, Montreal, Canada), indocyanine green (ICG) and its analogs (Licha, et al., 1996, SPIE 2927: 192-198; Ito et al., U.S. Pat. No. 5,968,479); indocyanines described in U.S. Pat. No. 6,448,008 (Caputo, 2002), indotricarbocyanine (ITC; WO 98/47538) and chelated lanthanide compounds. Fluorescent lanthanide metals include europium and terbium. Fluorescence properties of lanthanides are described in Lackowicz, 1999, Principles of Fluorescence Spectroscopy, 2.sup.nd Ed., Kluwar Academic, New York.

It is well known in the art that certain biomolecules such as albumin and transferrin, accumulate in solid tumors and can be used as carriers for the delivery of imaging and therapeutic agents to tumors and sites of inflammation (Becker et al. (2000) Photochem. Photobiol. 72:234-241; Kremer et al. (2000); 22:481-489; Schilling et al. (1992) 19:685-695; Nucl. Med. Biol. (2001) 28:895-902; Brasseur et al. (1999) Photochem. Photobiol 69:345-352; Gatter et al. (1983) J. Clin. Path. 36:539-545; Hamlin & Newman (1994) 26:45-56; Rennen et al. (2001) 28:401-408). This is due, in part, to the high density and increased permeability of the vasculature within many tumors and sites of inflammation. (Matsumura & Maeda (1986) Cancer Res. 46:6387-6392). Therefore in many pathologic conditions such as tumors, inflammation, and arteriosclerotic plaques, where the capillaries are "leaky", there are high local concentrations of albumin.

By virtue of this accumulation, the fluorophores of this invention can be used to image tumor tissues and sites of inflammation. The methods of the invention can therefore be used, for example, to determine the presence of tumor cells and localization of tumor cells, the presence and localization of inflammation, the presence and localization of vascular disease including areas at risk for acute occlusion (vulnerable plaques) in coronary and peripheral arteries and regions of expanding aneurysms. Alternatively, this accumulation can also be exploited to deliver specific fluorophores that are enzyme substrates, to interrogate for relatively more disease specific enzymes.

In one embodiment, the invention features an imaging construct comprising a fluorophore that has been designed to attach to an endogenous biocompatible molecule. The fluorophore is administered to the subject and the binding of the fluorophore to the biocompatible molecule occurs in situ in vivo. As a result of attachment to the biocompatible molecule, the fluorophore has a brighter signal intensity compared to the unbound fluorophore and also takes on some of the biological properties of the endogenous fluorophore attachment moiety, including the half-life.

In another embodiment, the biocompatible molecule is albumin. In another embodiment, the fluorophore may be pre-bound to the biocompatible molecule ex vivo. For example, the fluorophore may be mixed with sterile albumin or plasma replacement solution and the resulting mixture injected into the subject. Alternatively, blood may be drawn from the subject and the fluorophore can be mixed with the subject's blood and the resulting mixture re-injected into the subject.

Although the invention involves novel fluorophores, general principles of fluorescence, optical image acquisition, and image processing can be applied in the practice of the invention. For a review of optical imaging techniques, see, e.g., Alfano et al., 1997, "Advances in Optical Imaging of Biomedical Media," Ann. NY Acad. Sci., 820:248-270.

An imaging system useful in the practice of this invention typically includes three basic components: (1) an appropriate light source for fluorophore excitation, (2) a means for separating or distinguishing emissions from light used for fluorophore excitation, and (3) a detection system.

The light source provides monochromatic (or substantially monochromatic) near infrared light. The light source can be a suitably filtered white light, i.e., bandpass light from a broadband source. For example, light from a 150-watt halogen lamp can be passed through a suitable bandpass filter commercially available from Omega Optical (Brattleboro, Vt.). In some embodiments, the light source is a laser. See, e.g., Boas et al., 1994, Proc. Natl. Acad. Sci. USA 91:4887-4891; Ntziachristos et al., 2000, Proc. Natl. Acad. Sci. USA 97:2767-2772; Alexander, 1991, J. Clin. Laser Med. Surg. 9:416-418. Information on near infrared lasers for imaging can be found at various well-known sources.

A high pass or band pass filter (700 nm) can be used to separate optical emissions from excitation light. A suitable high pass or band pass filter is commercially available from Omega Optical.

In general, the light detection system can be viewed as including a light gathering/image forming component and a light detection/image recording component. Although the light detection system may be a single integrated device that incorporates both components, the light gathering/image forming component and light detection/image recording component will be discussed separately.

A particularly useful light gathering/image forming component is an endoscope. Endoscopic devices and techniques which have been used for in vivo optical imaging of numerous tissues and organs, including peritoneum (Gahlen et al., 1999, J. Photochem. Photobiol. B 52:131-135), ovarian cancer (Major et al., 1997, Gynecol. Oncol. 66:122-132), colon (Mycek et al., 1998, Gastrointest. Endosc. 48:390-394; Stepp et al., 1998, Endoscopy 30:379-386) bile ducts (Izuishi et al., 1999, Hepatogastroenterology 46:804-807), stomach (Abe et al., 2000, Endoscopy 32:281-286), bladder (Kriegmair et al., 1999, Urol. Int. 63:27-31; Riedl et al., 1999, J. Endourol. 13:755-759), and brain (Ward, 1998, J. Laser Appl. 10:224-228) can be employed in the practice of the present invention.

Other types of light gathering components useful in the invention are catheter based devices, including fiber optics devices. Such devices are particularly suitable for intravascular imaging. See, e.g., Tearney et al., 1997, Science 276:2037-2039; Proc. Natl. Acad. Sci. USA 94:4256-4261.

Still other imaging technologies, including phased array technology (Boas et al., 1994, Proc. Natl. Acad. Sci. USA 91:4887-4891; Chance, 1998, Ann. NY Acad. Sci. 38:29-45), diffuse optical tomography (Cheng et al., 1998, Optics Express 3:118-123; Siegel et al., 1999, Optics Express 4:287-298), intravital microscopy (Dellian et al., 2000, Br. J. Cancer 82:1513-1518; Monsky et al., 1999, Cancer Res. 59:4129-4135; Fukumura et al., 1998, Cell 94:715-725), and confocal imaging (Korlach et al., 1999, Proc. Natl. Acad. Sci. USA 96:8461-8466; Rajadhyaksha et al., 1995, J. Invest. Dermatol. 104:946-952; Gonzalez et al., 1999, J. Med. 30:337-356), Fluorescence Molecular Tomography (Ntziachristos V., *Nature Medicine* 8(7), 757-760 (2002). Monet, X., *Cancer Research* 65(14), 6330-6336 (2005), the IVIS® Imaging System, the SoftScan® and the eXplore Optix™ system can be employed in the practice of the present invention.

Any suitable light detection/image recording component, e.g., charge coupled device (CCD) systems or photographic film, can be used in the invention. The choice of light detection/image recording will depend on factors including type of light gathering/image forming component being used. Selecting suitable components, assembling them into a near infrared imaging system, and operating the system is within ordinary skill in the art.

The compounds (fluorophores) of the present invention and pharmaceutical compositions of the present invention can be administered orally, parentally, by inhalation, topically, rectally, nasally, buccally, vaginally, or via an implanted reservoir. The term "parental administration" includes intravenous, intramuscular, subcutaneous, intraarterial, intraarticular, intrasynovial, intrasternal, intrathecal, intraperitoneal, intracisternal, intrahepatic, intralesional, intracranial and intralymphatic injection or infusion techniques. The fluorophores of the present invention can also be administered via catheters or through a needle to a tissue.

In one embodiment, an effective amount (which is an amount effective to cause or increase fluorescence) of the compounds of the present invention are administered. In one embodiment, between about 1 ng/kg and about 100 mg/kg, between about 100 ng/kg and 10 mg/kg, between about 1 µg/kg and about 5 mg/kg, between about 10 µg/kg and about 2 mg/kg, between about 50 µg/kg and about 1 mg/kg of the compound of the present invention is administered.

The compounds of the present invention can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

The compounds of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

The term "alkyl" as used herein means a saturated straight-chain, branched or cyclic hydrocarbon. When straight-chained or branched, an alkyl group is typically C1-C20, more typically C1-C10; when cyclic, an alkyl group is typically C3-C12, more typically C3-C7. Examples of alkyl groups include methyl, ethyl, n-propyl, iso-propyl, n-butyl, sec-butyl and tert-butyl and 1,1-dimethylhexyl.

An "aliphatic group" is non-aromatic, and may optionally contain one or more units of unsaturation, e.g., double and/or triple bonds. An aliphatic group may be straight-chained or branched and typically contains between 1 and 12 carbon atoms, more typically between 1 and 6 carbon atoms, and even more typically between 1 and 4 carbon atoms. One or more methylene group in an aliphatic group can optionally be replaced by O, S, or NH.

As used herein the term non-aromatic carbocyclic ring or non-aromatic heterocyclic ring as used alone or as part of a larger moiety refers to a non-aromatic carbon or heteroatom containing ring which can be saturated or contain one or more units of unsaturation, having three to fourteen atoms including monocyclic and polycyclic rings in which the carbocyclic or heterocyclic ring can be fused to one or more non-aromatic carbocyclic or heterocyclic rings or one or more aromatic (carbocyclic or heterocyclic) rings.

The term "alkoxy" as used herein is represented by —OR, wherein R is an alkyl group as defined above.

The term "carbonyl" as used herein is represented by —C(═O)R, wherein R is an alkyl group as defined above.

The term "aromatic group" includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic). Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic).

The term non-aromatic heterocyclic group used alone or as part of a larger moiety refers to non-aromatic heterocyclic ring groups having three to fourteen members, including monocyclic heterocyclic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or contain one or more units of unsaturation. Examples of heterocyclic groups include piperidinyl, piperizinyl, pyrrolidinyl, pyrazolidinyl, imidazolidinyl, tetrahydroquinolinyl, inodolinyl, isoindolinyl, tetrahydrofuranyl, oxazolidinyl, thiazolidinyl, dioxolanyl, dithiolanyl, tetrahydropyranyl, dihydropyranyl, azepanyl and azetidinyl The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below. Preferably the nitrogen is unsubstituted.

A substituted aryl group as defined herein contains one or more substitutable ring atoms, such as carbon or nitrogen ring atoms. Examples of suitable substituents on a substitutable ring carbon atom of an aryl or aliphatic group include halogen (e.g., —Br, Cl, I and F), —OH, C1-C4 alkyl, C1-C4 haloalkyl, —NO$_2$, C1-C4 alkoxy, C1-C4 haloalkoxy, —CN, —NH$_2$, C1-C4 alkylamino, C1-C4 dialkylamino, —C(O)NH$_2$, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)$_2$, —NHC(O)O—(C1-C4 alkyl), —C(O)OH, —C(O)O—(C1-C4 alkyl), —NHC(O)NH$_2$, —NHC(O)NH(C1-C4 alkyl), —NHC(O)N(C1-C4 alkyl)$_2$, —NH—C(=NH)NH$_2$, —SO$_2$NH$_2$—SO$_2$NH(C1-C3alkyl), —SO$_2$N(C1-C3alkyl)$_2$, NHSO$_2$H, NHSO$_2$(C1-C4 alkyl) and aryl. Preferred substituents on aryl groups are as defined throughout the specification.

Examples of suitable substituents on a substitutable ring nitrogen atom of an aryl group include C1-C4 alkyl, NH$_2$, C1-C4 alkylamino, C1-C4 dialkylamino, —C(O)NH$_2$, —C(O)NH(C1-C4 alkyl), —C(O)(C1-C4 alkyl), —CO$_2$R, —C(O)C(O)R, —C(O)CH$_3$, —C(O)OH, —C(O)O—(C1-C4 alkyl), —SO$_2$NH$_2$—SO$_2$NH(C1-C3alkyl), —SO$_2$N(C1-C3alkyl)$_2$, NHSO$_2$H, NHSO$_2$(C1-C4 alkyl), —C(=S)NH$_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$, Substituted alkyl, aliphatic, non-aromatic carbocyclic or heterocyclic group as defined herein contain one or more substituents. Examples of suitable substituents for an alkyl group include those listed above for a substitutable carbon of an aryl and aliphatic and the following: =O, =S, =NNHR, =NN(R)$_2$, =NNHC(O)R, =NNHCO$_2$(alkyl), =NNHSO$_2$(alkyl), =NR, spiro cycloalkyl group or fused cycloalkyl group. R** in each occurrence, independently is —H or C1-C6 alkyl. Preferred substituents on alkyl aliphatic, non-aromatic carbocyclic or heterocyclic group groups are as defined throughout the specification.

Diagnostic and Disease Applications and Methods

The methods of the invention can be used to determine a number of indicia, including tracking the localization of the fluorophores and the resulting imaging agents in the subject over time or assessing changes or alterations in the metabolism and/or excretion of the molecules in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The invention can be used to help a physician or surgeon to identify and characterize areas of disease, such as arthritis, cancers and specifically colon polyps, or vulnerable plaque, to distinguish diseased and normal tissue, such as detecting tumor margins that are difficult to detect using an ordinary operating microscope, e.g., in brain surgery, help dictate a therapeutic or surgical intervention, e.g., by determining whether a lesion is cancerous and should be removed or non-cancerous and left alone, or in surgically staging or assessing a disease, e.g., intraoperative lymph node staging, sentinel lymph node mapping, or assessing intraoperative bleeding.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring drug therapy, including cell based therapies. The methods of the invention can also be used in prognosis of a disease or disease condition. Examples of such disease or disease conditions include inflammation (e.g., inflammation caused by arthritis, for example, rheumatoid arthritis), cancer (e.g., colorectal, ovarian, lung, breast, prostate, cervical, skin, brain, gastrointestinal, mouth, esophageal, bone), cardiovascular disease (e.g., atherosclerosis and inflammatory conditions of blood vessels, ischemia, stroke, thrombosis), dermatologic disease (e.g., Kaposi's Sarcoma, psoriasis), ophthalmic disease (e.g., macular degeneration, diabetic retinopathy), infectious disease (e.g., bacterial, viral, fungal and parasitic infections, including Acquired Immunodeficiency Syndrome), immunologic disease (e.g., an autoimmune disorder, lymphoma, multiple sclerosis, rheumatoid arthritis, diabetes mellitus), central nervous system disease (e.g., a neurodegenerative disease, such as Parkinson's disease or Alzheimer's disease), inherited diseases, metabolic diseases, environmental diseases (e.g., lead, mercury and radioactive poisoning, skin cancer), and bone-related disease (e.g., osteoporosis, primary and metastatic bone tumors, osteoarthritis). The methods of the invention can therefore be used, for example, to determine the presence of tumor cells and localization of tumor cells, the presence and localization of inflammation, including the presence of activated macrophages, for instance in atherosclerosis or arthritis, the presence and localization of vascular disease including areas at risk for acute occlusion (i.e., vulnerable plaques) in coronary and peripheral arteries, regions of expanding aneurysms, unstable plaque in carotid arteries, and ischemic areas. The methods and compounds (compositions) of the invention can also be used in identification and evaluation of apoptosis, necrosis, hypoxia and angiogenesis.

Optical imaging modalities and measurement techniques include, but are not limited to, fluorescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; intravital imaging; two photon imaging; interferometry; coherence interferometry; diffuse optical tomography and fluorescence molecular tomography, and measurement of light scattering, absorption, polarisation, luminescence, fluorescence lifetime, quantum yield, and quenching.

The compounds (compositions) and methods of the present invention can be used in combination with other imaging compositions and methods. For example, the methods of the present invention can be used in combination with other traditional imaging modalities such as X-ray, computed tomography (CT), positron emission tomography (PET), single photon computerized tomography (SPECT), and magnetic resonance imaging (MRI). For instance, the compounds (compositions) and methods of the present invention can be used in combination with CT and MR imaging to obtain both anatomical and biological information simultaneously, for example, by co-registration of a tomographic image with an image generated by another imaging modality. In particular, the combination with MRI or CT is preferable, given the high spatial resolution of these imaging techniques. The compounds (compositions) and methods of the present invention can also be used in combination with X-ray, CT, PET, SPECT and MR contrast agents or compounds (compositions) of the present invention may also contain components, such as iodine, gadolinium atoms and radioactive isotopes, which can be detected using CT, PET, SPECT, and MR imaging modalities in combination with optical imaging.

The invention also features in vivo optical imaging methods. In one embodiment the method includes the steps of: (a) administering to a subject a fluorophore; (b) allowing the fluorophore time to bind the biocompatible molecule in vivo and to reach the target tissue (c) illuminating the target tissue with light of a wavelength absorbable by the fluorophore; and (e) detecting the optical signal emitted by the fluorophore.

The invention also features in vivo optical imaging methods. In one embodiment the method includes the steps of: (a) administering to a subject a fluorophore pre-mixed with the biocompatible molecule; (b) allowing the fluorophore and resulting imaging agent time to reach the target tissue (c) illuminating the target tissue with light of a wavelength absorbable by the fluorophore; and (e) detecting the optical signal emitted by the fluorophore.

These steps can also be repeated at pre-determined intervals thereby allowing for the evaluation of emitted signal of the fluorophores in a subject over time. The emitted signal may take the form of an image. The subject may be a mammal, including a human, as well as other experimental animal models such as xenopus, zebrafish, and *C. elegans*.

The invention also features an in vivo method for selectively detecting and imaging two or more fluorophores simultaneously. The method includes administering to a subject two or more fluorophores, whose optical properties are distinguishable from that of the other. The method therefore, allows the recording of multiple events or targets.

Kits

The compounds (compositions) described herein can be packaged as a kit, which may optionally include instructions for using the fluorochromes or biocompatible fluorescent molecules in various exemplary applications. Non-limiting examples include kits that contain, e.g., the compounds (compositions) in a powder or lyophilized form, and instructions for using, including reconstituting, dosage information, and storage information for in vivo and/or in vitro applications. Kits may optionally contain containers of the compounds (compositions) in a liquid form ready for use, or requiring further mixing with solutions for administration. For in vivo applications, the kit may contain the compounds (compositions) in a dosage and form suitable for a particular application, e.g. a liquid in a vial, a topical creams, etc.

The kit can include optional components that aid in the administration of the unit dose to subjects, such as vials for reconstituting powder forms, syringes for injection, customized IV delivery systems, inhalers, etc. The kits may be supplied in either a container which is provided with a seal which is suitable for single or multiple puncturing with a hypodermic needle (e.g. a crimped-on septum seal closure) while maintaining sterile integrity. Such containers may contain single or multiple subject doses. Additionally, the unit dose kit can contain customized components that aid in the detection of the compounds (compositions) in vivo or in vitro, e.g., specialized endoscopes, light filters. The kits may also contain instructions for preparation and administration of the compounds (compositions). The kit may be manufactured as a single use unit dose for one subject, multiple uses for a particular subject; or the kit may contain multiple doses suitable for administration to multiple subjects ("bulk packaging"). The kit components may be assembled in cartons, blister packs, bottles, tubes, and the like.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The following non limiting examples demonstrate the synthesis of such near infrared fluorophores. Representative materials and methods that may be used in preparing the compounds of the invention are described further below. All chemicals and solvents (reagent grade) were used as commercially obtained without further purification. Dimethylformamide (DMF), acetonitrile, triethylammonium acetate, and triethylamine were commercially obtained. Diphenylpropylamine (DPPA) was obtained from Aldrich. The other intermediates are available from Matrix Scientific. The analytical and preparative HPLC methods generally utilized are:

A Column: Agilent Zorbax 80 Å, Extend C18, 4.6×250 mm (5 µm). Mobile Phase: Acetonitrile and 25 mM triethylammonium acetate.

B Column: Varian Dynamax, 100 Å, C18, 41.4×250 mm. Mobile Phase: Acetonitrile and 25 mM triethylammonium acetate.

C Column: Phenomenex Jupiter, 300 Å, C18 Mobile Phase Acetonitrile and 25 mM triethylammonium acetate.

Example 1

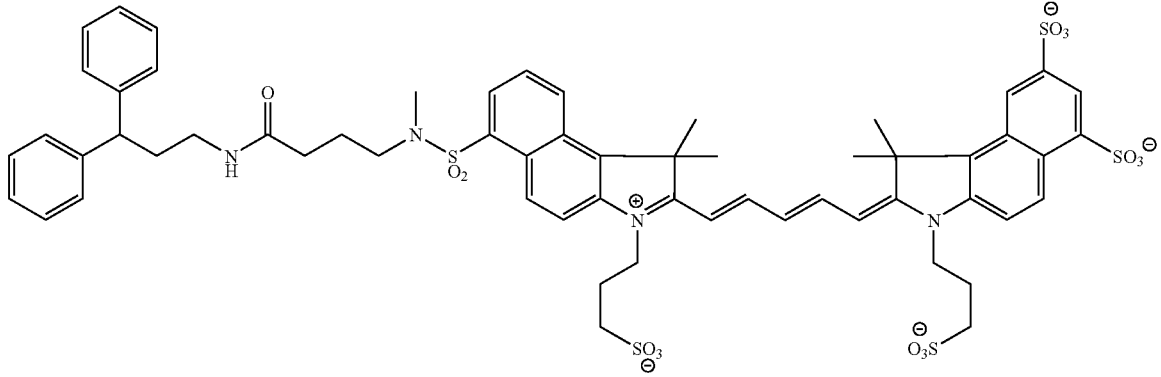

Synthesis of Example 1

The N-hydroxysuccinimidyl ester of the appropriate cyanine molecule (1.1 mg, 1 μmol) and 3,3-diphenylpropylamine (1.1 mg, 5 μmol, Aldrich) were combined in 115 μL of anhydrous DMF and kept at room temperature for one hour. The product was purified by RP-HPLC (25 mM triethylammonium acetate, pH 7 with an acetonitrile gradient of 20% to 85% over 20 minutes) and isolated as a lyophilized solid. ESI-MS m/e 1231.32065 [M]+ calculated for $C_{59}H_{67}N_4O_{15}S_5^+$, found 1231.3207.

Example 2

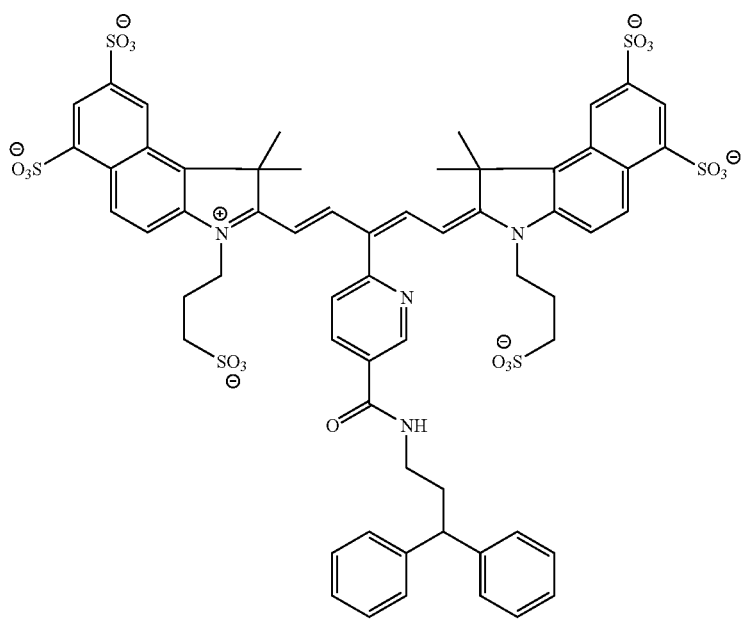

Synthesis of Example 2

N-hydroxysuccinimidyl ester of the appropriate cyanine molecule (1.1 mg, 1 μmol) and 3,3-diphenylpropylamine (1.1 mg, 5 μmol, Aldrich) were combined in 200 μL of anhydrous DMF and kept at room temperature for one hour. The product was purified by RP-HPLC (25 mM triethylammonium acetate, pH 7 with an acetonitrile gradient of 20% to 85% over 20 minutes) and isolated as a lyophilized solid. MALDI TOF: calc 1077.3 found 1077.9.

Example 3

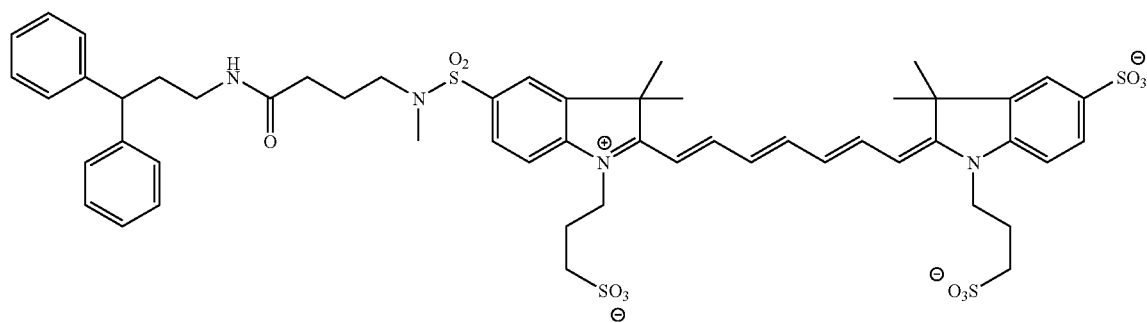

Synthesis of Example 3

N-hydroxysuccinimidyl ester of the appropriate cyanine molecule (1.0 mg, 1 μmol) and 3,3-diphenylpropylamine (1.1 mg, 5 μmol, Aldrich) were combined in 200 μL of anhydrous DMF and kept at room temperature for one hour. The product was purified by RP-HPLC (25 mM triethylammonium acetate, pH 7 with an acetonitrile gradient of 20% to 85% over 20 minutes) and isolated as a lyophilized solid. MS m/e: Calc=1333.2 found=1332.9.

Example 4

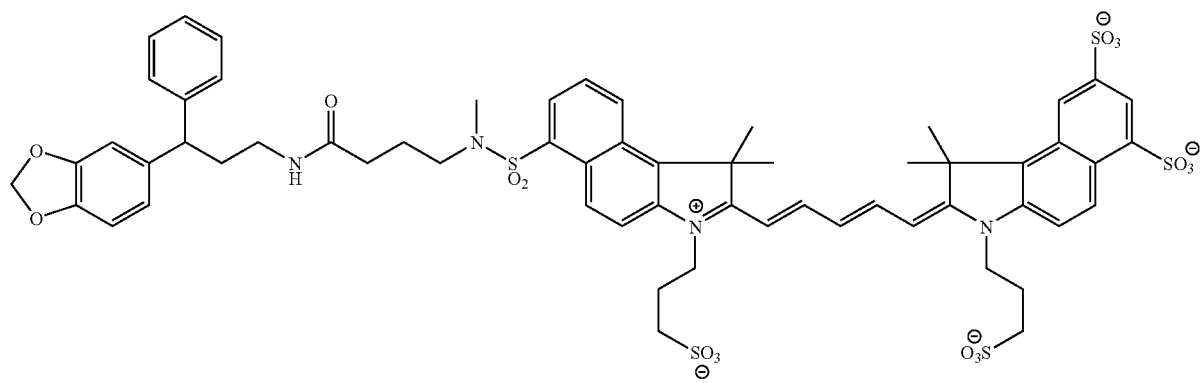

Synthesis of Example 4

N-hydroxysuccinimidyl ester of the appropriate cyanine molecule (1 μmol) and 3-benzo[1,3]-dioxol-5-yl-3-phenyl-propylamine (5 μmol, Aldrich) are combined in 100 μL of anhydrous DMF and kept at room temperature for one hour. The product is purified by RP-HPLC (25 mM triethylammonium acetate, pH 7 with an acetonitrile gradient of 20% to 85% over 20 minutes) and isolated as a lyophilized solid.

Example 5

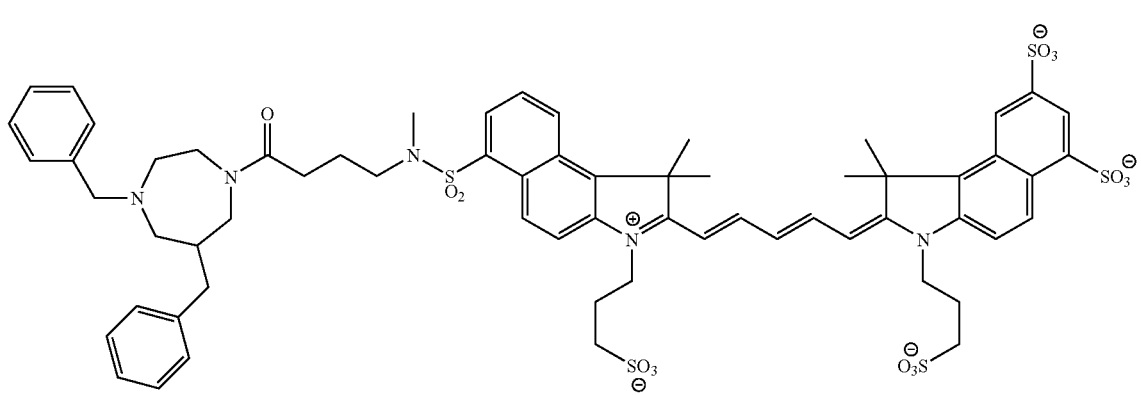

Synthesis of Example 5

N-hydroxysuccinimidyl ester of the appropriate cyanine molecule (1 µmol) and 1,6-dibenzyl-1,4-diazepane (5 µmol, Aldrich) are combined in 100 µL of anhydrous DMF and kept at room temperature for one hour. The product is purified by RP-HPLC (25 mM triethylammonium acetate, pH 7 with an acetonitrile gradient of 20% to 85% over 20 minutes) and isolated as a lyophilized solid.

Example 6

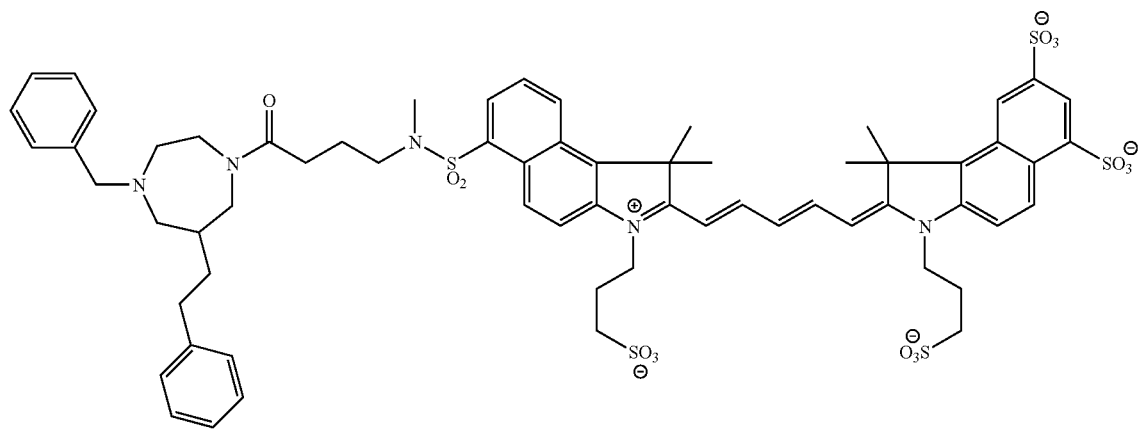

Synthesis of Example 6

N-hydroxysuccinimidyl ester of the appropriate cyanine molecule (1 µmol) and 1-benzyl-6,phenethyl-1,4-diazepane (5 µmol, Aldrich) are combined in 100 µL of anhydrous DMF and kept at room temperature for one hour. The product is purified by RP-HPLC (25 mM triethylammonium acetate, pH 7 with an acetonitrile gradient of 20% to 85% over 20 minutes) and isolated as a lyophilized solid.

Example 7

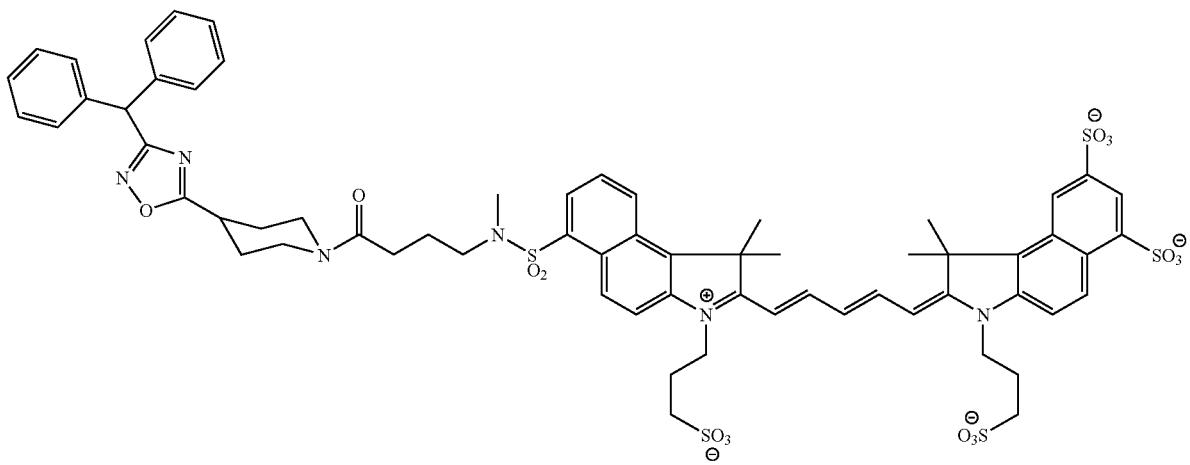

Synthesis of Example 7

N-hydroxysuccinimidyl ester of the appropriate cyanine molecule (1 μmol) and 4-[3-diphenylmethyl]-[1,2,4-oxadiazol-5-yl]-piperidine (5 μmol, Aldrich) are combined in 100 μL of anhydrous DMF and kept at room temperature for one hour. The product is purified by RP-HPLC (25 mM triethylammonium acetate, pH 7 with an acetonitrile gradient of 20% to 85% over 20 minutes) and isolated as a lyophilized solid.

Example 8

Synthesis of Example 8

N-hydroxysuccinimidyl ester of the appropriate cyanine molecule (1 μmol), diphenyl-piperidin-4-yl-methanol hydrochloride (5 μmol, Aldrich) and triethylamine (15 μmol) are combined in 100 μL of anhydrous DMF and kept at room temperature for one hour. The product is purified by RP-HPLC (25 mM triethylammonium acetate, pH 7 with an acetonitrile gradient of 20% to 85% over 20 minutes) and isolated as a lyophilized solid.

Example 9

Synthesis of Example 9

N-hydroxysuccinimidyl ester of the appropriate cyanine molecule (1 μmol), 4,4-diphenyl-piperidine hydrochloride (5 μmol, Aldrich) and triethylamine (15 μmol) are combined in 100 μL of anhydrous DMF and kept at room temperature for one hour. The product is purified by RP-HPLC (25 mM triethylammonium acetate, pH 7 with an acetonitrile gradient of 20% to 85% over 20 minutes) and isolated as a lyophilized solid.

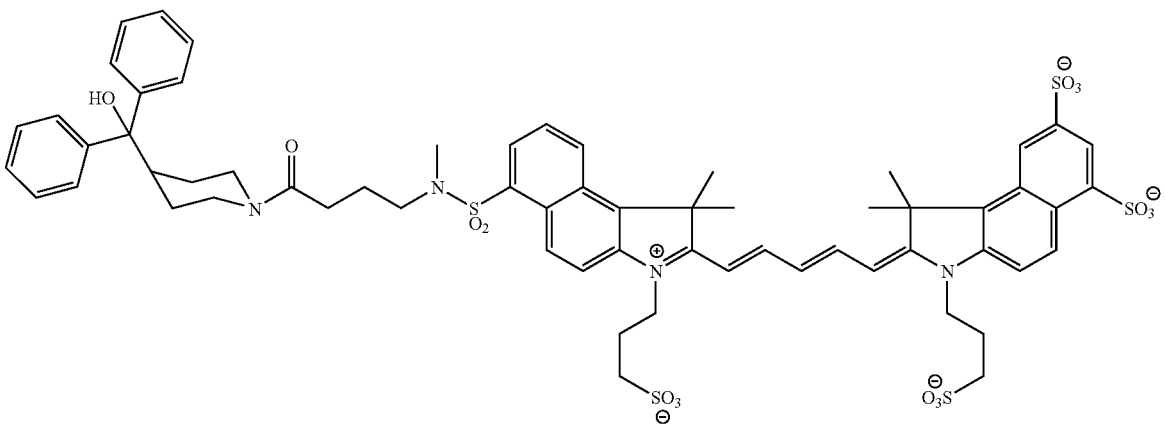

Example 10

The tumor cell line HT-29 (human colon carcinoma/HTB-38) was obtained from ATCC (Manassas, Va.). HT-29 cells were grown in McCoy's supplemented with 10% FBS at 37° C. in a humidified atmosphere containing 5% $CO_2$. Exponentially growing cells were trypsinized and re-suspended in Hank's Balanced Salt Solution at a concentration of $3\times10^7$ cells/ml. Female NU/NU mice 6-8 weeks old (Charles River Laboratory, Wilmington, Mass.) were injected subcutaneously with $3\times10^6$ HT-29 cells bilaterally in the first mammary fat pads. One week later, when tumors were approximately 30 $mm^3$, mice were injected intravenously with the molecule

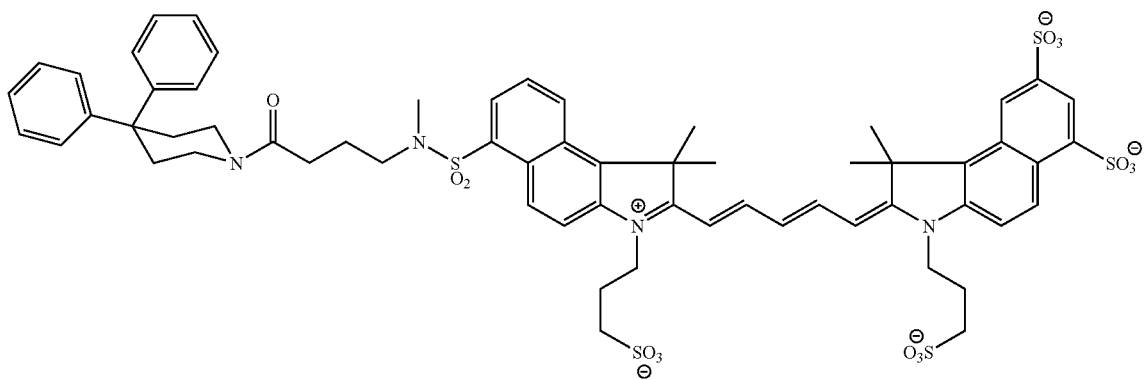

described in Example 1, (in 150 µl of 1×PBS) and imaged after 24 hrs on a fluorescence reflectance system (FRI, Kodak 2000MM) system.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of the following structural formula:

T-F, wherein, T is selected from the group consisting of

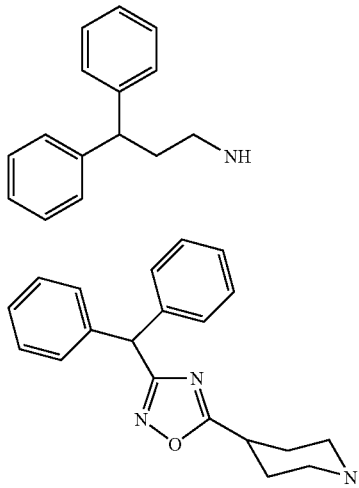

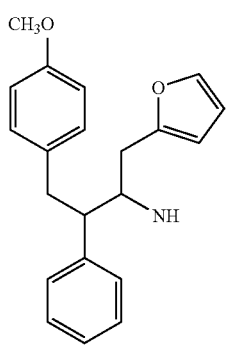

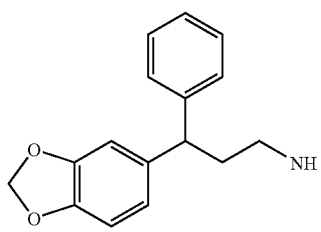

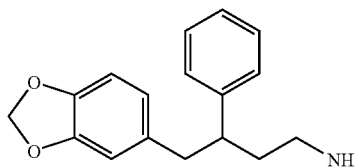

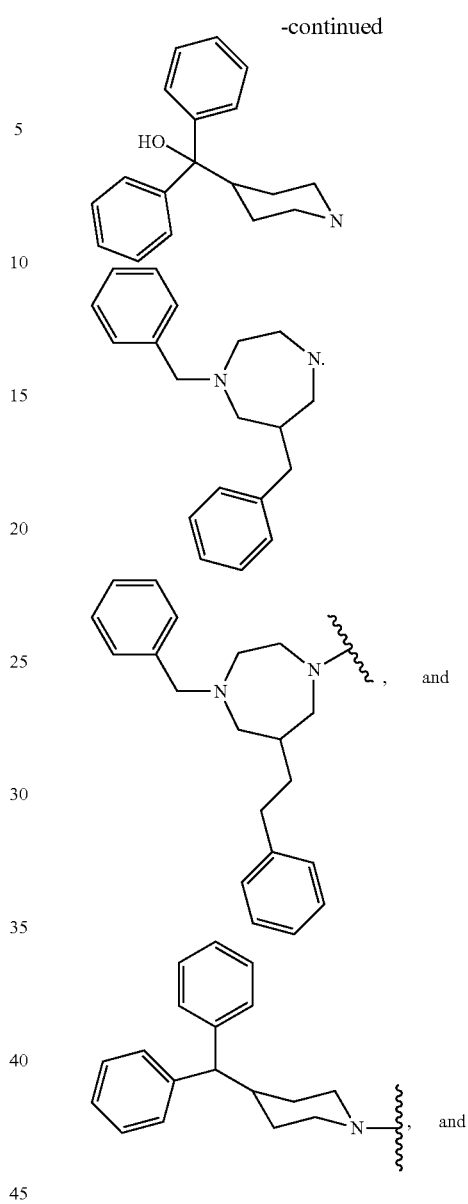

F is represented by the following structural formula (2):

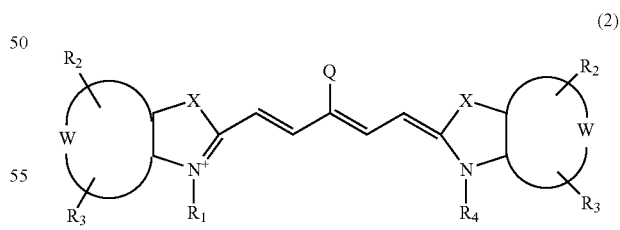

or a salt thereof, wherein:

X is independently selected from the group consisting of $C(CH_2Y_1)(CH_2Y_2)$, O, S, and Se;

$Y_1$ and $Y_2$ are independently selected from the group consisting of H, $C_1$-$C_{20}$ aliphatic group and a $C_1$-$C_{20}$ aliphatic group substituted with —OR*, N(R*)$_2$ or —SR*, wherein each R* is independently —H or $C_{1-20}$ alkyl;

W represents a benzo-condensed, a naphtho-condensed or a pyrido-condensed ring;

R₁ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;

R₄ is selected from the group consisting of $(CH_2)_xCH_3$, $(CH_2)_nSO_3^-$ and $(CH_2)_nSO_3H$, wherein x is an integer selected from 0 to 6 and n is an integer selected from 2 to 6;

R₂ and R₃ are independently selected from the group consisting of H, carboxylate, carboxylic acid, carboxylic ester, amine, amide, sulfonamide, hydroxyl, alkoxyl, a sulphonic acid moiety and a sulphonate moiety;

Q is selected from the group consisting of a heteroaryl ring substituted with a carboxyl group and a 6-membered heteroaryl ring substituted with a carbonyl group.

2. A compound of the following structural formula:

T-F wherein,

T is selected from the group consisting of

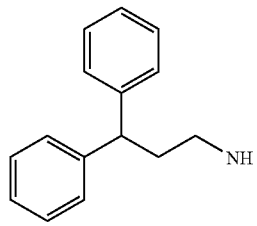

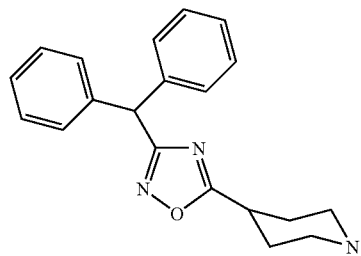

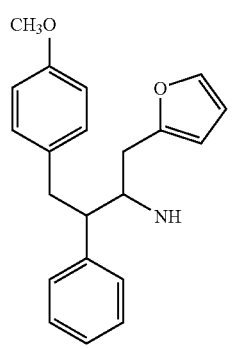

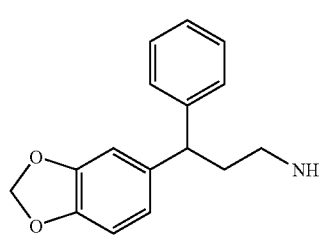

-continued

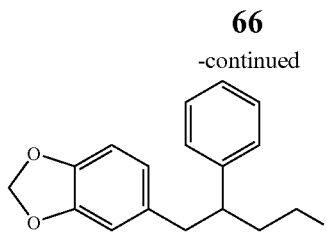

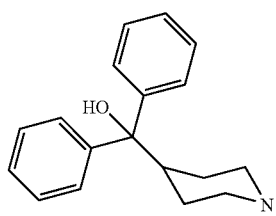

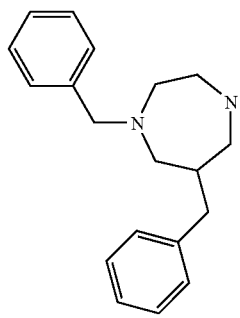

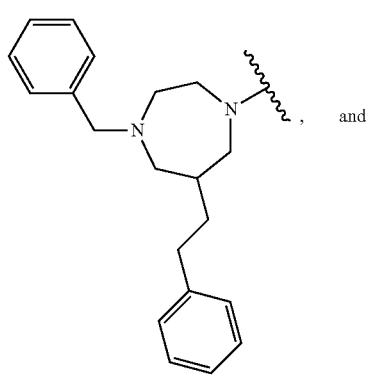, and

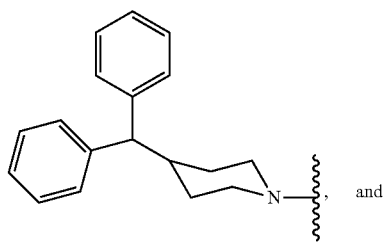, and

F is a fluorochrome of the structural formula:

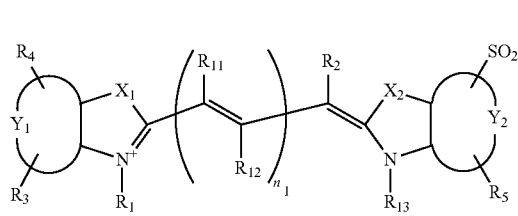

or a salt thereof, wherein:

$X_1$ and $X_2$ are independently selected from the group consisting of $C(CH_2K_1)(CH_2K_2)$, O, S and Se;

$K_1$ and $K_2$ are independently H or a $C_1$-$C_{20}$ aliphatic group; or $K_1$ and $K_2$ together are part of a substituted or unsubstituted carbocyclic or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, F, Br, Cl, $C_1$-$C_6$ alkyl, $C_1$-$C_6$ alkoxy, aryloxy, a nitrogen-containing heterocyclic ring, a sulfonate, an iminium ion, or any two adjacent $R_{12}$ and $R_{11}$ substituents, when taken in combination, form a 4-, 5-, or 6-membered carbocyclic ring optionally substituted one or more times by $C_1$-$C_6$ alkyl or halogen;

$R_1$ and $R_{13}$ are $(CH_2)_xCH_3$, wherein x is an integer selected from 0 to 6; or $R_1$ and $R_{13}$ are independently $(CH_2)_n SO_3$— or $(CH_2)_n SO_3H$ wherein n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of an unsubstituted $C_1$-$C_{20}$ aliphatic group, an unsubstituted aryl, and an unsubstituted alkylaryl;

Q is absent, a carbonyl group, or an unsubstituted $C_1$-$C_6$ alkyl group;

$R_7$ is selected from the group consisting of H, an unsubstituted $C_1$-$C_{20}$ aliphatic group, an unsubstituted aryl, an unsubstituted alkylaryl, wherein $R_7$ is optionally substituted with halogen; or $R_6$ and $R_7$, taken together form a 4-, 5-, 6- or 7-membered heterocyclic ring optionally substituted with halogen;

W is absent or is a group selected from the group consisting of —$SO_2NR_6$-Q-$CHR_7$—, —O—, —COO—, and —CONH—; and h=0-70; k=0 or 1; d=0-12; m=0-12; p=0-12.

3. The compound of claim 2, wherein Q is absent.

4. The compound of claim 2, wherein Q is $C_1$-$C_6$ alkyl.

5. The compound of claim 2, wherein Q is a carbonyl group.

6. A method of in vivo optical imaging of a tumor or a site of inflammation, the method comprising:
   (a) administering to a subject a compound of claim 1 or 2;
   (b) allowing the compound time to reach the tumor or the site of inflammation;
   (c) illuminating the subject with light of a wavelength absorbable by the fluorophore; and
   (d) detecting an optical signal emitted by the fluorophore.

7. The method of claim 6, wherein the signal emitted by fluorophore is used to construct an image.

8. The method of claim 6, wherein the subject is a mammal.

9. The method of claim 6, wherein the subject is a human.

10. The method of claim 6, wherein in step (a) two or more fluorophores whose signal properties are distinguishable are administered to a subject.

11. The method of claim 6, wherein the presence, absence, or level of signal emitted by the fluorophore is indicative of cancer or inflammation.

12. The method of claim 6, wherein the illuminating and detecting steps are done using an endoscope, catheter, planar optical systems, tomographic systems (including diffuse optical tomography), surgical goggles with attached bandpass filters, or intraoperative microscope.

13. The method of claim 6, wherein the method is used in detection of cancer or inflammation.

14. The method of claim 6, wherein the method is used in monitoring or dictating a therapeutic course of action for a treatment of cancer or inflammation.

15. A compound of formula (7)

(7)

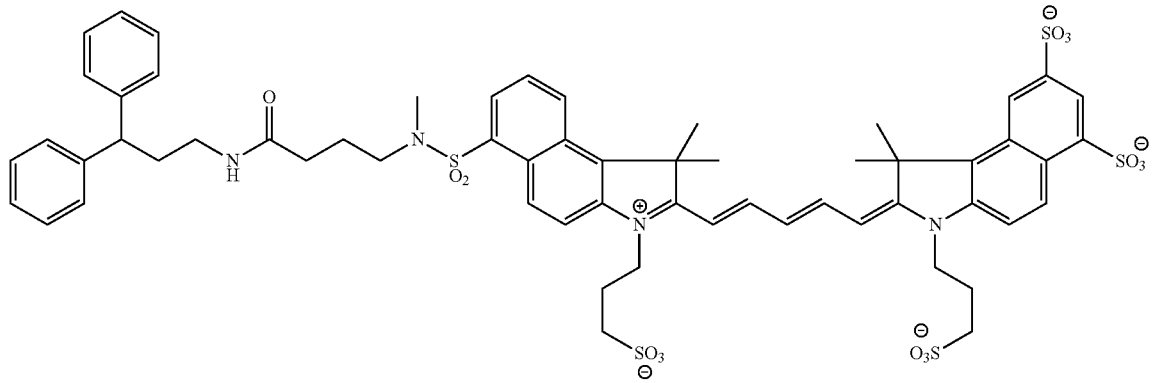

in the form of a salt.

* * * * *

UNITED STATES PATENT AND TRADEMARK OFFICE
CERTIFICATE OF CORRECTION

PATENT NO.       : 7,947,256 B2
APPLICATION NO.  : 12/065385
DATED            : May 24, 2011
INVENTOR(S)      : Milind Rajopadhye et al.

It is certified that error appears in the above-identified patent and that said Letters Patent is hereby corrected as shown below:

Claim number 1, column 63, lines 20-25, replace

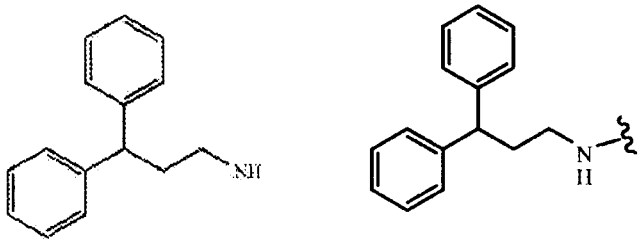

with

Claim number 1, column 63, lines 30-39, replace

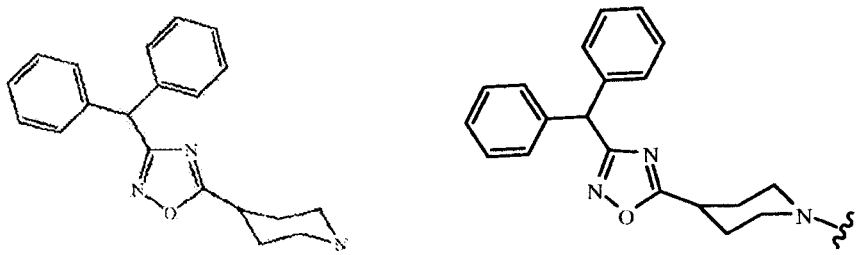

with

Signed and Sealed this
Twelfth Day of July, 2011

David J. Kappos
*Director of the United States Patent and Trademark Office*

CERTIFICATE OF CORRECTION (continued)
U.S. Pat. No. 7,947,256 B2

Claim number 1, column 63, lines 40-49, replace

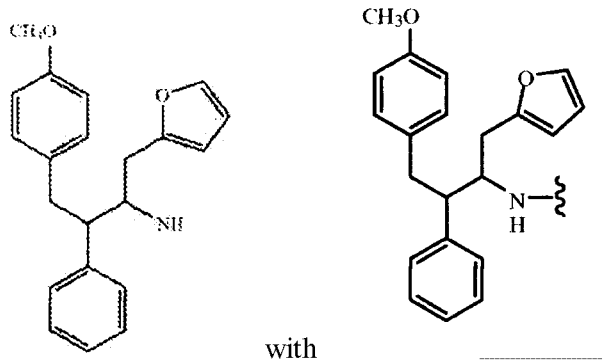

with

Claim number 1, column 63, lines 50-59, replace

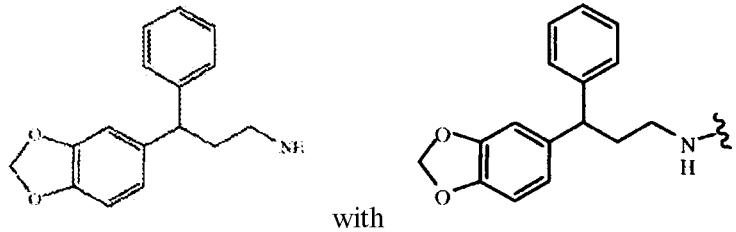

with

Claim number 1, column 63, lines 60-65, replace

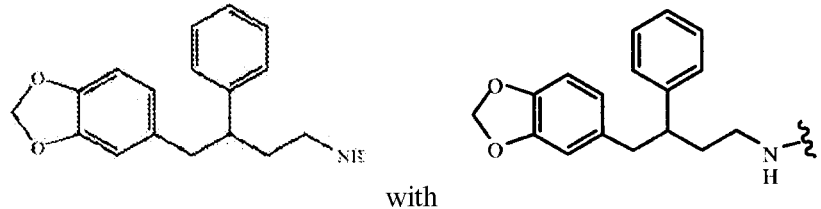

with

Claim number 1, column 64, lines 1-10, replace

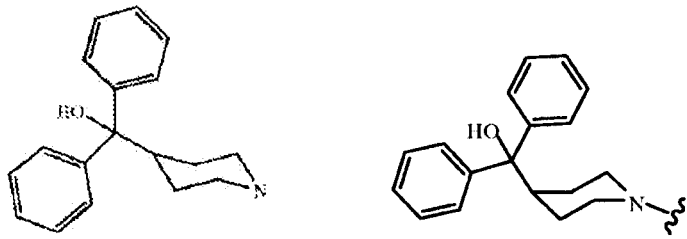

with

Claim number 1, column 64, lines 10-20, replace

CERTIFICATE OF CORRECTION (continued)
U.S. Pat. No. 7,947,256 B2

Page 3 of 4

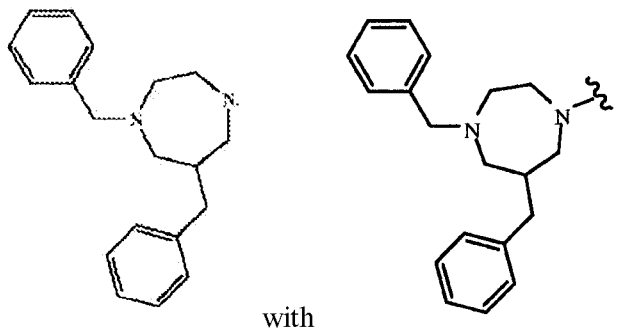

with

Claim number 2, column 65, lines 21-30, replace

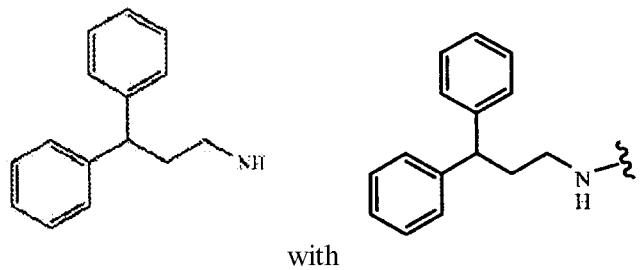

with

Claim number 2, column 65, lines 31-43, replace

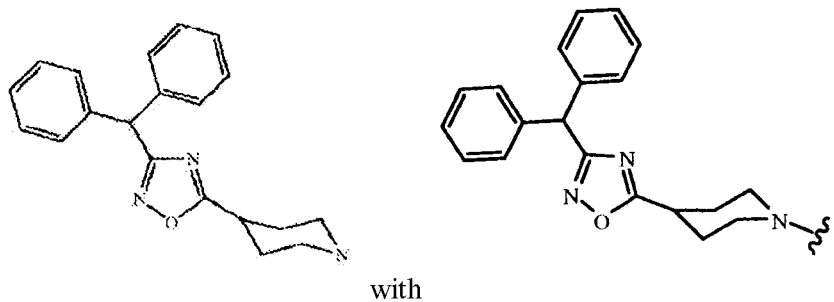

with

Claim number 2, column 65, lines 45-55, replace

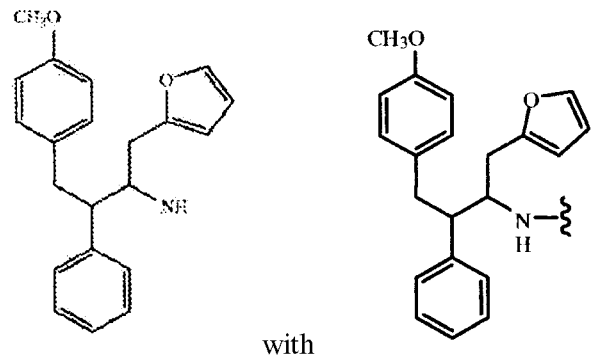

with

Claim number 2, column 65, lines 56-65, replace

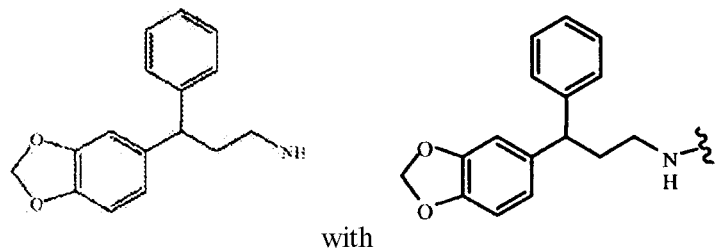
with
Claim number 2, column 66, lines 1-10, replace
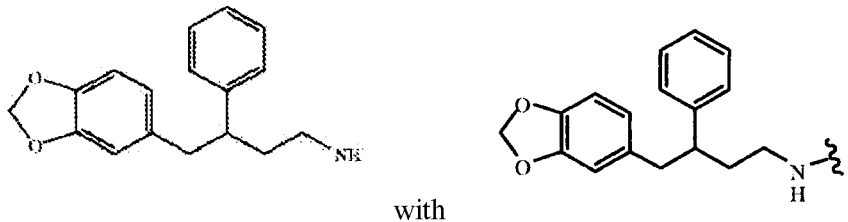
with
Claim number 2, column 66, lines 11-20, replace
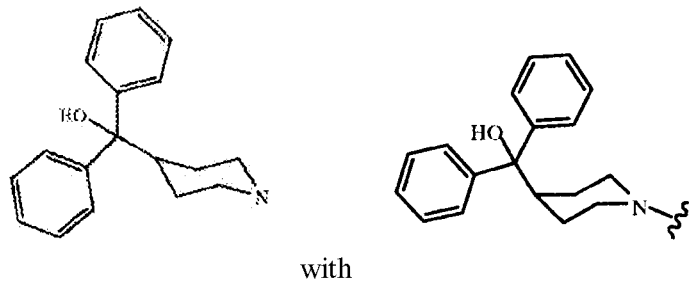
with
Claim number 2, column 66, lines 21-35, replace
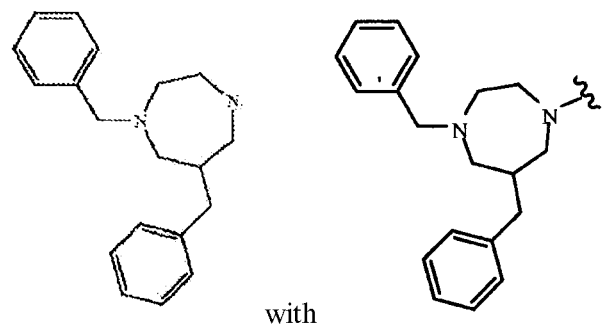
with
Claim number 2, column 67, lines 30-31, replace (CH$_2$)$_n$SO$_3$– with (CH$_2$)$_n$SO$_3^-$.